US009403814B2

(12) United States Patent
Zhang et al.

(10) Patent No.: US 9,403,814 B2
(45) Date of Patent: Aug. 2, 2016

(54) CRYSTALLINE FORMS OF DIHYDROPYRIMIDINE DERIVATIVES

(71) Applicant: SUNSHINE LAKE PHARMA CO., LTD., Dongguan, Guangdong (CN)

(72) Inventors: Yingjun Zhang, Dongguan (CN); Qingyun Ren, Dongguan (CN); Xinchang Liu, Dongguan (CN); Chaolei Wang, Dongguan (CN); Tianming Wang, Dongguan (CN); Siegfried Goldmann, Wuppertal (DE)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 14/420,666

(22) PCT Filed: Sep. 27, 2013

(86) PCT No.: PCT/CN2013/084383
§ 371 (c)(1),
(2) Date: Feb. 10, 2015

(87) PCT Pub. No.: WO2014/048355
PCT Pub. Date: Apr. 3, 2014

(65) Prior Publication Data
US 2015/0239877 A1    Aug. 27, 2015

(30) Foreign Application Priority Data

Sep. 27, 2012  (CN) .......................... 2012 1 0369019
Apr. 4, 2013   (CN) .......................... 2013 1 0117076

(51) Int. Cl.
*C07D 417/04* (2006.01)

(52) U.S. Cl.
CPC .................................. *C07D 417/04* (2013.01)

(58) Field of Classification Search
CPC ....................................................... C07D 417/04
See application file for complete search history.

(56) References Cited

U.S. PATENT DOCUMENTS 7,381,729 B2    6/2008  Pahl et al.
RE44,987 E      7/2014  Goldmann et al.

FOREIGN PATENT DOCUMENTS

| CN | 101744823 B     | 6/2013  |
| WO | WO2008154818 A1 | 12/2008 |
| WO | WO2008154819 A1 | 12/2008 |
| WO | WO2008154820 A1 | 12/2008 |
| WO | WO2010069147 A1 | 6/2010  |

OTHER PUBLICATIONS

English translation of CN101744823, published Jun. 2013.*
International Search Report of PCT/CN2013/084383.
Written Opinion of PCT/CN2013/084383.
David P. Elder et. al. "The utility of sulfonate salts in drug development", Journal of Pharmaceutical Sciences, Jul. 2010,pp. 2948-2961,vol. 99, No. 7.
Mino R.Caira, "Crystalline polymorphism or organic compounds", Topics in current chemistry, Jan. 1, 1998, pp. 163-208, vol. 198.
Extended European Search report, Feb. 5, 2016.

\* cited by examiner

*Primary Examiner* — Rebecca Anderson
*Assistant Examiner* — Karen Cheng
(74) *Attorney, Agent, or Firm* — Kam W. Law; Squire Patton Boggs (US) LLP

(57) ABSTRACT

The present invention relates to crystalline forms of dihydropyrimidine derivatives, and pharmaceutical compositions comprising the crystalline forms disclosed herein, which may be used for preventing, managing, treating or lessening the severity of a viral disease in a patient, especially hepatitis B infection or a disease caused by hepatitis B infection.

28 Claims, 12 Drawing Sheets

CRYSTALLINE FORMS OF DIHYDROPYRIMIDINE DERIVATIVES

CROSS-REFERENCE TO RELATED APPLICATIONS

This is a U.S. national stage application of the International Patent Application No. PCT/CN2013/084383, filed Sep. 27, 2013, which claims priorities to Chinese Patent Application No. 201210369019.4, filed Sep. 27, 2012, and No. 201310117076.8, filed Apr. 4, 2013, all of which are incorporated herein by reference in their entireties.

FIELD OF THE INVENTION

The present invention relates to crystalline forms of dihydropyrimidine derivatives, and pharmaceutical compositions comprising the crystalline forms or tautomers thereof disclosed herein, which may be used for preventing, managing, treating or lessening the severity of a viral disease in a patient, wherein the viral disease is hepatitis B infection or a disease caused by hepatitis B infection.

BACKGROUND OF THE INVENTION

Chemical Stability, Solid State Stability and "Storage Duration" of drug substance are particularly important factors in the manufacture of a medicament. The form identification of drugs which can be convenient manufacture, preparation and applied to patients is very important. Ideal drug substances and a combination thereof can be stored effectively during the evaluation period, and there are no obvious changes in physical and chemical properties (e.g., chemical composition, density, water absorbing rate, solubility and dissolution rate, etc.) of the active constituent.

A known amorphous form drug substance cannot solve the above problems well. For instance, an amorphous form drug substance is difficult to be managed and prepared, its solubility is unreliable and the chemical and physical property is usually unstable.

Therefore, if Technology R&D Specialists find a stable crystalline form during the drug development process, many of the above problems can be resolved. In the preparation of commercially available and pharmaceutically acceptable pharmaceutical compositions, if possible, providing medication in crystalline and stable form is important. However, the targets describe herein are not always achieved. Actually, it is usually impossible to predict crystallization behaviors and results of compounds only based on the molecular structure, the useful results can be obtained need to do a great amount of experimental explorations.

Patent WO 2008/154817 discloses a series of compounds which are used for preventing, managing, treating or lessening the severity of viral diseases in a patient, especially hepatitis B infection or a disease caused by hepatitis B infection. Patent WO 2008/154817 discloses specific compound 4[R,S]-ethyl 4-(2-bromo-4-fluorophenyl)-6-(morpholinomethyl)-2-(thiazol-2-yl)-1,4-dihydropyrimidine-5-carboxylate (formula (II)), and the compound of formula (II) simultaneously has the tautomer 6[R,S]-ethyl 6-(2-bromo-4-fluorophenyl)-4-(morpholinomethyl)-2-(thiazol-2-yl)-1,6-dihydropyrimidine-5-carboxylate (formula (IIa)). The compound and the tautomer have higher transforming speed at ambient temperature, which exists as the structure of 4 [R,S]-ethyl4-(2-bromo-4-fluorophenyl)-6-(morpholinomethyl)-2-(thiazol-2-yl)-1,4-dihydropyrimidine-5-carboxylate at ambient temperature. Formulae (II) and (IIa) are as shown below:

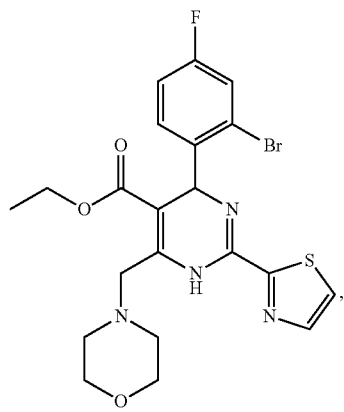

(II)

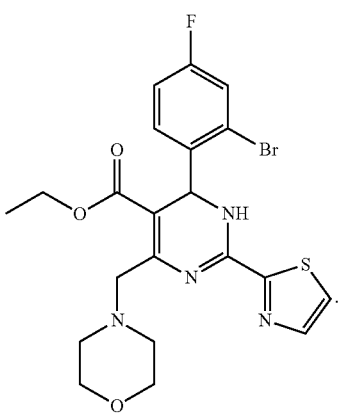

(IIa)

SUMMARY OF THE INVENTION

Studying on the X-ray single crystal diffraction patterns of the compound of formula (II) and methanesulfonic acid salt thereof, the present invention discovers that the salt exists as the structure of 6[R,S]-ethyl 6-(2-bromo-4-fluorophenyl)-4-(morpholinomethyl)-2-(thiazol-2-yl)-1,6-dihydro pyrimidine-5-carboxylate mesylate (formula (I)). Formulae (I) and (Ia) are as shown below:

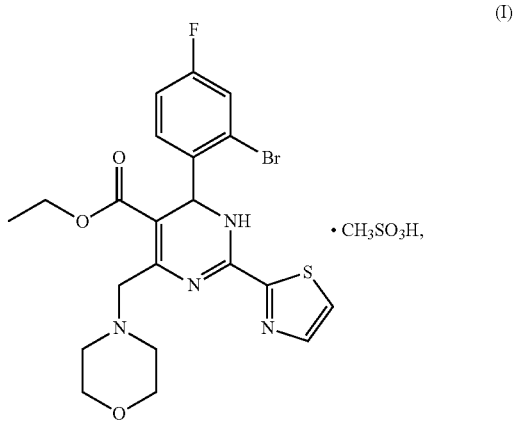

(I)

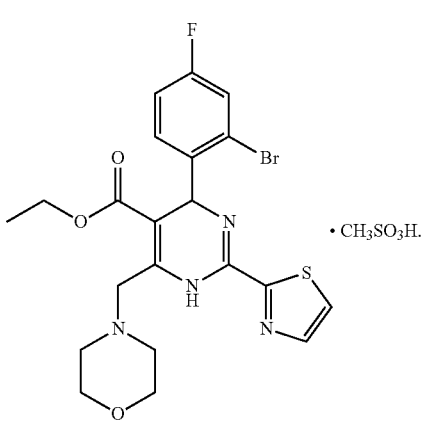

(Ia)

6[R,S]-ethyl 6-(2-bromo-4-fluorophenyl)-4-(morpholinomethyl)-2-(thiazol-2-yl)-1,6-dihydropyrimidine-5-carboxylate mesylate (formula (I)) has excellent solubility, stability and druggability compared to the free molecular (formula (II)) and other common form of salts thereof.

In one aspect, provided herein are crystalline forms of the compound represented by formula (I), a tautomer (formula (Ia)) or a combination thereof base on a great amount of experiments.

In another aspect, the crystalline form of the compound represented by formula (I) is form A, form B, form C, form G, form H, form I or a combination thereof.

In some embodiments, the crystalline form is form A having an X-ray powder diffraction (XRPD) pattern comprising peaks expressed in degrees 2θ at 6.57°±0.2°, 13.13°±0.2°, 13.38°±0.2°, 19.73°±0.2°, 20.18°±0.2°, 20.90°±0.2°, 24.90°±0.2°, 26.63°±0.2° and 29.01°±0.2°.

In some embodiments, the crystalline form is form A having an X-ray powder diffraction (XRPD) pattern comprising peaks expressed in degrees 2θ at 6.57°±0.2°, 13.13°±0.2°, 13.38°±0.2°, 19.73°±0.2°, 20.18°±0.2°, 20.90°±0.2°, 22.43°±0.2°, 24.38°±0.2°, 24.90°±0.2°, 26.63°±0.2°, 27.93°±0.2° and 29.01°±0.2°.

In some embodiments, the crystalline form is form A having an X-ray powder diffraction (XRPD) pattern comprising peaks expressed in degrees 2θ at 6.57°±0.2°, 9.73°±0.2°, 11.14°±0.2°, 13.13°±0.2°, 13.38°±0.2°, 19.73°±0.2°, 20.18°±0.2°, 20.90°±0.2°, 22.43°±0.2°, 23.20°±0.2°, 24.38°±0.2°, 24.90°±0.2°, 26.63°±0.2°, 27.93°±0.2°, 29.01°±0.2°, 29.84°±0.2°, 30.78°±0.2° and 31.68°±0.2°.

In some embodiments, the crystalline form is form A having an X-ray powder diffraction (XRPD) pattern substantially the same as shown in FIG. 1.

In some embodiments, the crystalline form is form A having a differential scanning calorimetry (DSC) thermogram comprising an endothermic peak at about 162.3° C.±3° C.

In some embodiments, the crystalline form is form A having a differential scanning calorimetry (DSC) thermogram substantially the same as shown in FIG. 2.

In some aspect, provided herein is a pharmaceutical composition comprising the crystalline form A and a pharmaceutically acceptable carrier, excipient, diluent, adjuvant, vehicle or a combination thereof.

In another aspect, provided herein is use of the crystalline form A or the pharmaceutical composition comprising the crystalline form A for the manufacture of a medicament for preventing, managing, treating or lessening the severity of hepatitis B infection and a disorder caused by hepatitis B infection in a patient.

In some embodiments, the crystalline form is form B having an X-ray powder diffraction (XRPD) pattern comprising peaks expressed in degrees 2θ at 6.68°±0.2°, 13.39°±0.2°, 19.65°±0.2°, 20.26°±0.2°, 22.45°±0.2°, 24.80°±0.2°, 25.01°±0.2°, 26.19°±0.2°, 26.61°±0.2° and 28.79°±0.2°.

In some embodiments, the crystalline form is form B having an X-ray powder diffraction (XRPD) pattern comprising peaks expressed in degrees 2θ at 6.68°±0.2°, 9.77°±0.2°, 9.98°±0.2°, 11.88°±0.2°, 13.39°±0.2°, 16.65°±0.2°, 17.66°±0.2°, 19.08°±0.2°, 19.65°±0.2°, 20.26°±0.2°, 20.81°±0.2°, 20.97°±0.2°, 22.45°±0.2°, 24.80°±0.2°, 25.01°±0.2°, 26.19°±0.2°, 26.61°±0.2°, 28.79°±0.2°, 29.78°±0.2°, 30.13°±0.2°, 31.61°±0.2°, 31.92°±0.2° and 32.45°±0.2°.

In some embodiments, the crystalline form is form B having an X-ray powder diffraction (XRPD) pattern comprising peaks expressed in degrees 2θ at 6.68°±0.2°, 9.77°±0.2°, 9.98°±0.2°, 11.88°±0.2°, 13.39°±0.2°, 14.62°±0.2°, 16.65°±0.2°, 17.66°±0.2°, 19.08°±0.2°, 19.65°±0.2°, 20.26°±0.2°, 20.81°±0.2°, 20.97°±0.2°, 22.07°±0.2°, 22.45°±0.2°, 24.80°±0.2°, 25.01°±0.2°, 25.45°±0.2°, 26.19°±0.2°, 26.61°±0.2°, 27.85°±0.2°, 28.15°±0.2°, 28.79°±0.2°, 29.35°±0.2°, 29.78°±0.2°, 30.13°±0.2°, 30.51°±0.2°, 31.29°±0.2°, 31.61°±0.2°, 31.92°±0.2°, 32.45°±0.2° and 35.41°±0.2°.

In some embodiments, the crystalline form is form B having an X-ray powder diffraction (XRPD) pattern substantially the same as shown in FIG. 3.

In some embodiments, the crystalline form is form B having a differential scanning calorimetry (DSC) thermogram comprising an endothermic peak at about 165.8° C.±3° C.

In some embodiments, the crystalline form is form B having a differential scanning calorimetry (DSC) thermogram substantially the same as shown in FIG. 4.

In some aspect, provided herein is a pharmaceutical composition comprising the crystalline form B and a pharmaceutically acceptable carrier, excipient, diluent, adjuvant, vehicle or a combination thereof.

In another aspect, provided herein is use of the crystalline form B or a pharmaceutical composition comprising the crystalline form B for the manufacture of a medicament for preventing, managing, treating or lessening the severity of hepatitis B infection or a disorder caused by hepatitis B in a patient.

In some embodiments, the crystalline form is form C having an X-ray powder diffraction (XRPD) pattern comprising peaks expressed in degrees 2θ at 5.39°±0.2°, 13.25°±0.2°, 16.00°±0.2°, 17.27°±0.2°, 21.33°±0.2°, 21.92°±0.2°, 22.53°±0.2°, 23.47°±0.2°, 26.56°±0.2°, 26.87°±0.2°, 29.41°±0.2° and 32.22°±0.2°.

In some embodiments, the crystalline form is form C having an X-ray powder diffraction (XRPD) pattern comprising peaks expressed in degrees 2θ at 5.39°±0.2°, 13.25°±0.2°, 16.00°±0.2°, 17.27°±0.2°, 20.31°±0.2°, 21.33°±0.2°, 21.92°±0.2°, 22.53°±0.2°, 23.47°±0.2°, 23.58°±0.2°, 26.56°±0.2°, 26.87°±0.2°, 29.41°±0.2°, 30.52°±0.2°, 31.35°±0.2°, 32.05°±0.2° and 32.22°±0.2°.

In some embodiments, the crystalline form is form C having an X-ray powder diffraction (XRPD) pattern comprising peaks expressed in degrees 2θ at 5.39°±0.2°, 10.42°±0.2°, 10.69°±0.2°, 12.04°±0.2°, 13.25°±0.2°, 13.56°±0.2°, 16.00°±0.2°, 17.27°±0.2°, 19.61°±0.2°, 19.86°±0.2°, 20.02°±0.2°, 20.31°±0.2°, 21.33°±0.2°, 21.92°±0.2°, 22.17°±0.2°, 22.29°±0.2°, 22.53°±0.2°, 23.47°±0.2°, 23.58°±0.2°, 24.35°±0.2°, 24.96°±0.2°, 25.10°±0.2°, 26.39°±0.2°, 26.56°±0.2°, 26.87°±0.2°, 27.25°±0.2°, 27.64°±0.2°, 29.41°±0.2°, 29.90°±0.2°, 30.31°±0.2°, 30.52°±0.2°, 31.35°±0.2°, 32.05°±0.2°, 32.22°±0.2°, 32.96°±0.2°, 33.71°±0.2°, 34.11°±0.2°, 34.88°±0.2°, 36.23°±0.2° and 36.46°±0.2°.

In some embodiments, the crystalline form is form C having an X-ray powder diffraction (XRPD) pattern substantially the same as shown in FIG. 5.

In some embodiments, the crystalline form is form C having a differential scanning calorimetry (DSC) thermogram comprising an endothermic peak at about 172.6° C.±3° C.

In some embodiments, the crystalline form is form C having a differential scanning calorimetry (DSC) thermogram substantially the same as shown in FIG. 6.

In some aspect, provided herein is a pharmaceutical composition comprising the crystalline form C and a pharmaceutically acceptable carrier, excipient, diluent, adjuvant, vehicle or a combination thereof.

In another aspect, provided herein is use of the crystalline form C or a pharmaceutical composition comprising the crystalline form C for the manufacture of a medicament for preventing, managing, treating or lessening the severity of hepatitis B infection and a disorder caused by hepatitis B infection in a patient.

In some embodiments, the crystalline form is form G having an X-ray powder diffraction (XRPD) pattern comprising peaks expressed in degrees 2θ at 16.47°±0.2°, 19.40°±0.2°, 20.61°±0.2°, 22.37°±0.2°, 22.82°±0.2°, 23.21°±0.2°, 25.66°±0.2°, 25.94°±0.2°, 26.87°±0.2°, 27.02°±0.2°, 28.11°±0.2° and 30.27°±0.2°.

In some embodiments, the crystalline form is form G having an X-ray powder diffraction (XRPD) pattern comprising peaks expressed in degrees 2θ at 9.99°±0.2°, 10.30°±0.2°, 16.47°±0.2°, 17.30°±0.2°, 19.40°±0.2°, 20.61°±0.2°, 21.26°±0.2°, 22.37°±0.2°, 22.82°±0.2°, 23.21°±0.2°, 23.58°±0.2°, 25.66°±0.2°, 25.94°±0.2°, 26.87°±0.2°, 27.02°±0.2°, 27.18°±0.2°, 28.11°±0.2°, 28.40°±0.2°, 29.98°±0.2°, 30.27°±0.2°, 31.14°±0.2°, 32.42°±0.2°, 33.11°±0.2° and 33.34°±0.2°.

In some embodiments, the crystalline form is form G having an X-ray powder diffraction (XRPD) pattern comprising peaks expressed in degrees 2θ at 7.07°±0.2°, 7.80°±0.2°, 9.99°±0.2°, 10.30°±0.2°, 11.14°±0.2°, 14.20°±0.2°, 15.36°±0.2°, 16.47°±0.2°, 17.30°±0.2°, 19.40°±0.2°, 19.73°±0.2°, 19.85°±0.2°, 20.40°±0.2°, 20.61°±0.2°, 21.26°±0.2°, 22.37°±0.2°, 22.82°±0.2°, 23.21°±0.2°, 23.58°±0.2°, 23.83°±0.2°, 24.58°±0.2°, 25.66°±0.2°, 25.94°±0.2°, 6.87°±0.2°, 27.02°±0.2°, 27.18°±0.2°, 27.79°±0.2°, 28.11°±0.2°, 28.40°±0.2°, 29.98°±0.2°, 30.27°±0.2°, 30.66°±0.2°, 31.14°±0.2°, 32.11°±0.2°, 22.42°±0.2°, 32.76°±0.2°, 33.11°±0.2° and 33.34°±0.2°.

In some embodiments, the crystalline form is form G having an X-ray powder diffraction (XRPD) pattern substantially the same as shown in FIG. 7.

In some embodiments, the crystalline form is form G having a differential scanning calorimetry (DSC) thermogram comprising an endothermic peak at about 134.3° C.±3° C.

In some embodiments, the crystalline form is form G having a differential scanning calorimetry (DSC) thermogram substantially the same as shown in FIG. 8.

In some aspect, provided herein is a pharmaceutical composition comprising the crystalline form G and a pharmaceutically acceptable carrier, excipient, diluent, adjuvant, vehicle or a combination thereof.

In another aspect, provided herein is use of the crystalline form G or a pharmaceutical composition comprising the crystalline form G for the manufacture of a medicament for preventing, managing, treating or lessening the severity of hepatitis B infection and a disorder caused by hepatitis B infection in a patient.

In some embodiments, the crystalline form is form H having an X-ray powder diffraction (XRPD) pattern comprising peaks expressed in degrees 2θ at 7.58°±0.2°, 10.20°±0.2°, 12.00°±0.2°, 19.07°±0.2°, 19.93°±0.2°, 20.78°±0.2°, 21.33°±0.2°, 21.48°±0.2°, 24.76°±0.2°, 25.59°±0.2°, 25.82°±0.2°, 26.01°±0.2° and 26.58°±0.2°.

In some embodiments, the crystalline form is form H having an X-ray powder diffraction (XRPD) pattern comprising peaks expressed in degrees 2θ at 7.58°±0.2°, 10.29°±0.2°, 12.00°±0.2°, 14.78°±0.2°, 17.69°±0.2°, 18.32°±0.2°, 19.07°±0.2°, 19.93°±0.2°, 20.13°±0.2°, 20.78°±0.2°, 21.33°±0.2°, 21.48°±0.2°, 22.60°±0.2°, 24.40°±0.2°, 24.58°±0.2°, 24.76°±0.2°, 25.59°±0.2°, 25.82°±0.2°, 26.01°±0.2°, 26.58°±0.2°, 27.15°±0.2°, 27.31°±0.2°, 27.49°±0.2°, 27.78°±0.2°, 31.69°±0.2° and 31.98°±0.2°.

In some embodiments, the crystalline form is form H having an X-ray powder diffraction (XRPD) pattern comprising peaks expressed in degrees 2θ at 7.58°±0.2°, 10.29°±0.2°, 12.00°±0.2°, 14.78°±0.2°, 15.83°±0.2°, 16.49°±0.2°, 17.69°±0.2°, 18.32°±0.2°, 19.07°±0.2°, 19.24°±0.2°, 19.93°±0.2°, 20.13°±0.2°, 20.78°±0.2°, 21.33°±0.2°, 21.48°±0.2°, 21.88°±0.2°, 22.35°±0.2°, 22.60°±0.2°, 23.37°±0.2°, 23.77°±0.2°, 24.40°±0.2°, 24.58°±0.2°, 24.76°±0.2°, 25.59°±0.2°, 25.82°±0.2°, 26.01°±0.2°, 26.58°±0.2°, 27.15°±0.2°, 27.31°±0.2°, 27.49°±0.2°, 27.78°±0.2°, 29.28°±0.2°, 29.77°±0.2°, 30.17°±0.2°, 31.69°±0.2°, 31.98°±0.2°, 32.30°±0.2° and 33.28°±0.2°.

In some embodiments, the crystalline form is form H having an X-ray powder diffraction (XRPD) pattern substantially the same as shown in FIG. 9.

In some embodiments, the crystalline form is form H having a differential scanning calorimetry (DSC) thermogram comprising an endothermic peak at about 132.1° C.±3° C.

In some embodiments, the crystalline form is form H having a differential scanning calorimetry (DSC) thermogram substantially the same as shown in FIG. 10.

In some aspect, provided herein is a pharmaceutical composition comprising the crystalline form H and a pharmaceutically acceptable carrier, excipient, diluent, adjuvant, vehicle or a combination thereof.

In another aspect, provided herein is use of the crystalline form H or a pharmaceutical composition comprising the crystalline form H for the manufacture of a medicament for preventing, managing, treating or lessening the severity of hepatitis B infection and a disorder caused by hepatitis B infection in a patient.

In some embodiments, the crystalline form is form I having an X-ray powder diffraction (XRPD) pattern comprising peaks expressed in degrees 2θ at 9.41°±0.2°, 17.59°±0.2°, 21.37°±0.2°, 21.72°±0.2°, 22.15°±0.2°, 22.50°±0.2°, 23.90°±0.2°, 24.59°±0.2°, 24.99°±0.2°, 26.32°±0.2°, 27.09°±0.2°, 29.68°±0.2° and 30.53°±0.2°.

In some embodiments, the crystalline form is form I having an X-ray powder diffraction (XRPD) pattern comprising peaks expressed in degrees 2θ at 9.41°±0.2°, 10.13°±0.2°, 12.64°±0.2°, 13.04°±0.2°, 17.59°±0.2°, 21.37°±0.2°, 21.72°±0.2°, 21.90°±0.2°, 22.15°±0.2°, 22.50°±0.2°, 23.76°±0.2°, 23.90°±0.2°, 24.59°±0.2°, 24.99°±0.2°, 26.32°±0.2°, 26.95°±0.2°, 27.09°±0.2°, 27.90°±0.2°, 28.54°±0.2°, 29.10°±0.2°, 29.68°±0.2°, 30.53°±0.2°, 32.18°±0.2° and 33.03°±0.2°.

In some embodiments, the crystalline form is form I having an X-ray powder diffraction (XRPD) diagram comprising peaks expressed in degrees 2θ at 4.41°±0.2°, 9.26°±0.2°, 9.41°±0.2°, 10.13°±0.2°, 11.25°±0.2°, 12.64°±0.2°, 13.04°±0.2°, 17.59°±0.2°, 18.29°±0.2°, 20.17°±0.2°, 20.29°±0.2°, 21.37°±0.2°, 21.72°±0.2°, 21.90°±0.2°, 22.15°±0.2°, 22.50°±0.2°, 23.76°±0.2°, 23.90°±0.2°, 24.59°±0.2°, 24.99°±0.2°, 25.71°±0.2°, 26.32°±0.2°, 26.95°±0.2°, 27.09°±0.2°, 27.66°±0.2°, 27.90°±0.2°, 28.54°±0.2°, 29.10°±0.2°, 29.68°±0.2°, 30.53°±0.2°, 30.93°±0.2°, 32.18°±0.2°, 33.03°±0.2° and 33.56°±0.2°.

In some embodiments, the crystalline form is form I having an X-ray powder diffraction (XRPD) pattern substantially the same as shown in FIG. 11.

In some embodiments, the crystalline form is form I having a differential scanning calorimetry (DSC) thermogram comprising an endothermic peak at about 82.0° C.±3° C.

In some embodiments, the crystalline form is form I having a differential scanning calorimetry (DSC) thermogram substantially the same as shown in FIG. 12.

In some aspect, provided herein is a pharmaceutical composition comprising the crystalline form I and a pharmaceutically acceptable carrier, excipient, diluent, adjuvant, vehicle or a combination thereof.

In another aspect, provided herein is use of the crystalline form I or a pharmaceutical composition comprising the crystalline form I for the manufacture of a medicament for preventing, managing, treating or lessening the severity of hepatitis B infection and a disorder caused by hepatitis B infection in a patient.

And provided herein is a pharmaceutical composition comprising a crystalline form disclosed herein, such as form A, form B, form C, form G, form H, form I, or a tautomer or a combination thereof; and a pharmaceutically acceptable carrier, excipient, diluent, adjuvant, vehicle or a combination thereof.

Also provided herein is use of a crystalline form disclosed herein, or a tautomer a combination thereof or a pharmaceutical composition for the manufacture of a medicament for preventing, managing, treating or lessening a viral disease in a patient.

In certain embodiments, the use is disclosed herein, wherein the viral disease is hepatitis B infection or a disease caused by hepatitis B infection.

In other embodiments, the use is disclosed herein, wherein the disease caused by hepatitis B infection is cirrhosis or hepatocellular carcinoma.

In another aspect, provided herein is a method of preventing, managing, treating or lessening the severity of viral diseases in a patient comprising administering to the patient with a therapeutically effective amount of a crystalline form or a pharmaceutical composition disclosed herein.

In certain embodiments, the method is disclosed herein, wherein the viral disease is hepatitis B infection or a disease caused by hepatitis B infection.

In other embodiments, the methods is disclosed herein, wherein the disease caused by hepatitis B infection is cirrhosis or hepatocellular carcinoma.

In another aspect, provided herein is a crystalline form disclosed herein, or a tautomer or a combination thereof or a pharmaceutical compositions for use in preventing, managing, treating or lessening a viral disease.

In certain embodiments, a crystalline form disclosed herein, or a tautomer or a combination thereof or a pharmaceutical compositions is disclosed herein, wherein the viral disease is hepatitis B infection or a disease caused by hepatitis B infection.

In other embodiments, a crystalline form disclosed herein, or a tautomer a combination thereof or a pharmaceutical compositions is disclosed herein, wherein the disease caused by hepatitis B infection is cirrhosis or hepatocellular carcinoma.

And provided herein is use of the crystalline forms disclosed herein, a combination thereof or the pharmaceutical compositions for the manufacture of a medicament for preventing, managing, treating or lessening the severity of hepatitis B infection or a disease caused by hepatitis B infection, comprising administering to the patient with a therapeutically effective amount of the medicament.

As is well known, in the area of X-ray powder diffraction (XRPD), relative peak height of XRPD pattern depends on many factors related to sample preparation and geometric shapes of the instrument, while peak position is relatively insensitive to experimental details. Therefore, in some embodiments, the crystalline compounds disclosed herein characterized by XRPD pattern with some peak positions, have essentially the same characteristics as XRPD pattern provided in appended drawings of the present invention. According to the state of the instrument for the experiment. The error margin in 2θ of the characteristic peaks is ±0.2°.

Similarly, as is well known in the area of differential scanning calorimetry (DSC), relative peak height of DSC thermogram depends on many factors related to sample preparation and geometric shapes of the instrument, while peak position is relatively insensitive to experiment details. Therefore, in some embodiments, the crystalline compounds disclosed herein characterized by DSC thermogram with some peak positions, have essentially the same characteristics as DSC thermogram provided in appended drawings of the present invention. According to the state of the instrument for the experiment. The error margin in the melting peaks is ±3° C.

Whenever a number having a value N is disclosed, any number having the value N±0.01, N±0.02, N±0.03, N±0.05, N±0.07, N±0.08, N±0.1, N±0.15 N±0.2, N±1, N±2, N±1.5, N±3, NA, N±5, N±6, N±7, N±8, N±9, N±10, N±15, or N±20 is specifically disclosed, wherein "±" refers to plus or minus. Whenever a numerical range with a lower limit, RL, and an upper limit, RU, is disclosed, any number falling within the range is specifically disclosed.

The novel crystalline form of 6[R,S]-ethyl 6-(2-bromo-4-fluorophenyl)-4-(morpholinomethyl)-2-(thiazol-2-yl)-1,6-dihydro pyrimidine-5-carboxylate mesylate disclosed herein is substantially pure, wherein the crystalline form is form A, form B, form C, form G, form H or form I.

As used herein, the X-axis of X-ray powder diffraction (XRPD) pattern is 2θ in degrees.

As used herein, an X-ray powder diffraction (XRPD) pattern or a differential scanning calorimetry (DSC) thermogram that is "substantially the same as shown" in a figure refers to an X-ray powder diffraction (XRPD) pattern or a differential scanning calorimetry (DSC) thermogram having at least 50%, at least 60%, at least 70%, at least 80%, at least 90%, at least 95%, or at least 99% of the peaks shown in the figure.

As used herein, a crystalline form that is "substantially pure" refers to a crystalline form that is substantially free of one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms, based on the total volume or weight of the crystalline form and the one or more other crystalline forms.

As used herein, a crystalline form that is "substantially free" of one or more other crystalline forms refers to a crystalline form containing less than 20%, less than 10%, less than 5%, less than 4%, less than 3%, less than 2%, less than 1%, less than 0.5%, less than 0.1%, or less than 0.01% of the one or more other crystalline forms, based on the total volume or weight of the crystalline form and the one or more other crystalline forms.

As used herein, the term "relative intensity" refers to the intensity of a peak with respect to the intensity of the strongest peak in the X-ray powder diffraction (XRPD) pattern which is regarded as 100%.

As used herein, the term "combination" refers to a crystalline form containing a tautomer thereof, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; a crystalline form containing one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or a crystalline form containing other crystalline forms, i.e., the other crystalline forms have less than 20%, less than 10%, less than 5%, less than 3%, less than 1%, less than 0.5%, less than 0.1%, or less than 0.01% of the crystalline form, based on the total volume or weight of the crystalline form and one or more other crystalline forms.

As used herein, when referring to a spectrum and/or to data presented in a graph, the term "peak" refers to a feature that one skilled in the art would recognize as not attributable to background noise.

As used herein, all numbers disclosed herein are approximate values, regardless whether the word "about" is used in connection therewith. The value of each number may differ by 1%, 2%, 5%, 7%, 8%, 10%, 15% or 20%. Therefore, whenever a number having a value N is disclosed, any number having the value N+/−1%, N+/−2%, N+/−3%, N+/−5%, N+/−7%, N+/−8%, N+/−10%, N+/−15% or N+/−20% is specifically disclosed, wherein "+/−" refers to plus or minus. Whenever a numerical range with a lower limit, RL, and an upper limit, RU, is disclosed, any number falling within the range is specifically disclosed. In particular, the following numbers within the range are specifically disclosed: R=RL+K*(RU−RL), wherein K is a variable ranging from 1% to 100% with a 1% increment, i.e., K is 1%, 2%, 3%, 4%, 5%, . . . , 50%, 51%, 52%, . . . , 95%, 96%, 97%, 98%, 99%, or 100%. Moreover, any numerical range defined by two R numbers as defined above is also specifically disclosed.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

Stereochemical definitions and conventions used herein generally follow Parker, et al., McGraw-Hill Dictionary of Chemical Terms (1984) McGraw-Hill Book Company, New York and Eliel, et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy,* 21st ed., 2005, Lippincott Williams & Wilkins, Philadelphia, and Swarbrick et al., *Encyclopedia of Pharmaceutical Technology*, eds. 1988-1999, Marcel Dekker, New York, all of which are herein incorporated by reference in their entireties, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, aluminum, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, topically, buccally, or via an explanted reservoir. The term "parenteral" as used herein includes subcutaneous, intravenous, intramuscular, intra-articular, intrasynovial, intrasternal, intrathecal, intraocular, intrahepatic, intralesional and intracranial injection or infusion techniques. In some embodiments, the compositions are preferred to be administered orally, intraperitoneally or intravenously. Sterile injectable forms of the compositions disclosed herein include aqueous or oleaginous suspension. These suspensions may be formulated according to techniques known in the art using suitable dispersing or wetting agents and suspending agents.

The pharmaceutically acceptable compositions disclosed herein can be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, microorganism, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or calcium phosphate and/or a) fillers or extenders such as starches, lactose, sucrose, glucose, mannitol, and silicic acid; b) binders such as carboxymethylcellulose, alginates, gelatin, povidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

EXAMPLES

Figure 1:
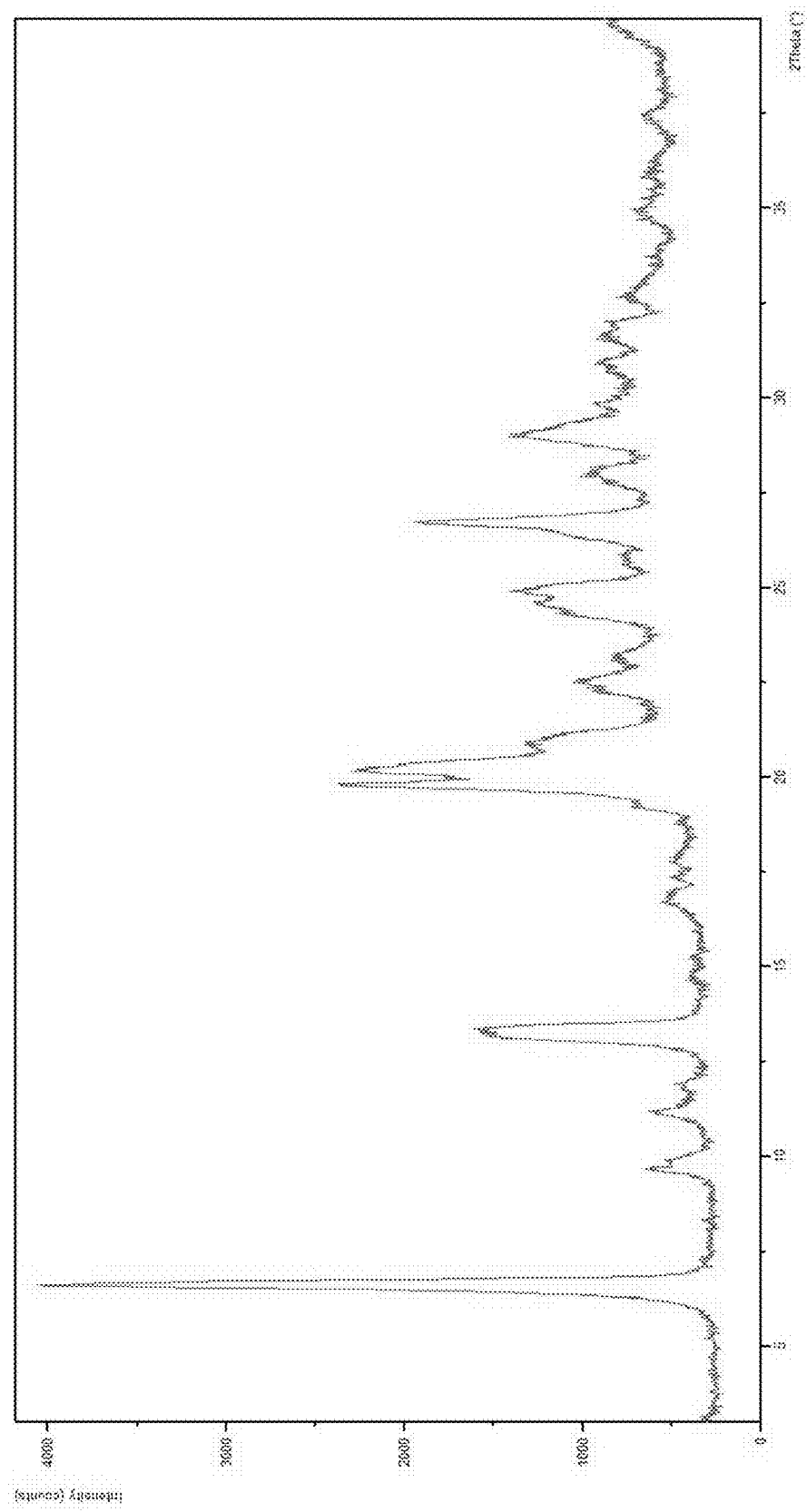
FIG. 1 shows the X-ray powder diffraction (XRPD) pattern of the crystalline form A of dihydropyrimidine derivative which is prepared according to the present invention.

The invention is illustrated further by the following examples, which are not be construed as limiting the invention in scope.

Said crystalline forms according to the invention were characterized by X-ray powder diffraction (XRPD) and differential scanning calorimetry (DSC) as shown below.

X-Ray Powder Diffraction (XRPD): X-ray powder diffraction diagram is recorded on a PANalytical Empyrean X-ray diffractometer using Cu-Kα radiation (45 KV, 40 mA). A thin layer is prepared from powder sample on the single-crystal silicon wafer, and a sample spinner is used. The angular range extends from 0° to 40° in 2θ with a 0.0168° step size in 2θ.

Differential Scanning calorimetry (DSC): Differential scanning calorimetry thermogram is recorded on a TA Q2000 instrument with a thermoanalysis controller. The data is collected and analyzed by TA Instruments Thermal Solutions software. About 1-5 mg sample is weighed accurately in special aluminium pans with a cover lid, and heated under dry nitrogen purge. The scan rate is 10° C./minute and the sample is heated from ambient temperature to 200° C.

Example 1

The preparation of amorphous 6[R,S]-ethyl 6-(2-bromo-4-fluoro phenyl)-4-(morpholinomethyl)-2-(thiazol-2-yl)-1,6-dihydropyrimidine-5-carboxylate mesylate (compound Z)

A 1000 mL eggplant-shaped bottle equipped with a magnetic stirrer was charged with 4 [R,S]-ethyl 4-(2-bromo-4-fluorophenyl)-6-(morpholinomethyl)-2-(thiazol-2-yl)-1,4-dihydropyrimidine-5-carboxylate (100 g, 196 mmol, the compound was synthesized according to the procedures described in patent WO 2008/154817) and acetone (600 mL). The stirred suspension was heated to reflux until all solid had dissolved followed by filtration. The filtrate was added slowly to methanesulfonic acid (25.5 mL, 392 mmol), and the color of the solution gradually deepened. The color finally changed to orange from yellow. The solution was stirred further for 1 hour and concentrated in vacuo. The residue was dissolved in dichloromethane (1000 mL), and the solution was washed with brine after clarification, dried over anhydrous sodium sulfate and concentrated in vacuo to afford a foam solid, which was dried in a vacuum oven at 55° C. to give the product as a yellow solid (76.8 g, 64.8%). The compound was characterized by the following spectroscopic data:

$^1$H-NMR (400 MHz, DMSO-$d_6$) δ (ppm): 10.18 (br.s, 1H), 9.67 (br.s, 1H), 8.13 (br.s, 1H), 8.09 (d, 1H), 7.31-7.61 (m, 3H), 6.02 (s, 1H), 4.63 (d, 1H), 4.58 (d, 1H), 4.03 (q, 2H), 3.97 (br.s, 4H), 3.49 (br.s, 4H), 2.32 (s, 3H), 1.10 (t, 3H).

Example 2

The Preparation of Crystalline Form A

A 500 mL eggplant-shaped bottle was charged with 4[R, S]-ethyl 4-(2-bromo-4-fluorophenyl)-6-(morpholinomethyl)-2-(thiazol-2-yl)-1,4-dihydropyrimidine-5-carboxylate (5 g, 9.8 mmol, the compound was synthesized according to the procedures described in patent WO 2008/154817) and 2,2-dimethoxypropane (200 mL). The suspension was heated at 90° C. under $N_2$ until all solid had dissolved, and the solution was then added to methanesulfonic acid (1.88 g, 19.6 mmol) dropwise. The mixture was stirred for 4 hours under reflux. By cooling the reaction mixture to room temperature, crystals precipitated, and were collected by filtration, washed with 2,2-dimethoxypropane and dried in a vacuum oven at 55° C. to give the product as a yellow solid (2.9 g, 48.9%).

The Identification of Crystalline Form A

1) The XRPD pattern of crystalline form A was analyzed and identified by using Empyrean X-ray powder diffraction (XRPD) with Cu-Kα radiation, having the following characteristic peaks expressed in degrees 2θ at 6.57°, 9.73°, 11.14°, 13.13°, 13.38°, 19.73°, 20.18°, 20.90°, 22.43°, 23.20°, 24.38°, 24.90°, 26.63°, 27.93°, 29.01°, 29.84°, 30.78° and 31.68°. The error margin in 2θ of the characteristic peaks is ±0.2°.

2) The DSC thermogram of crystalline form A was analyzed and identified by using TA Q2000 differential scanning calorimetry (DSC) with a scan rate of 10° C./minute, comprising an endothermic peak at 162.3° C. The error margin in the melting peaks is ±3° C.

Example 3

The Preparation of Crystalline Form B

A 1000 mL eggplant-shaped bottle was charged with 4[R, S]-ethyl 4-(2-bromo-4-fluorophenyl)-6-(morpholinomethyl)-2-(thiazol-2-yl)-1,4-dihydropyrimidine-5-carboxylate (5 g, 9.8 mmol, the compound was synthesized according to the procedures described in patent WO 2008/154817) and isopropyl ether (500 mL). The suspension was heated at 75° C. under $N_2$ until all solid had dissolved, and the solution was added to methanesulfonic acid (2.35 g, 24.5 mmol) dropwise. The mixture was stirred for 3 hours under reflux. By cooling the reaction mixture to room temperature, crystals precipi- tated, and were collected by filtration, washed with isopropyl ether and dried in a vacuum oven at 50° C. to give the product as a yellow solid (3.3 g, 55.6%).

The Identification of Crystalline Form B

1) The XRPD pattern of crystalline form was analyzed and identified by using Empyrean X-ray powder diffraction (XRPD) with Cu-Kα radiation, having the following characteristic peaks expressed in degrees 2θ at 6.68°, 9.77°, 9.98°, 11.88°, 13.39°, 14.62°, 16.65°, 17.66°, 19.08°, 19.65°, 20.26°, 20.81°, 20.97°, 22.07°, 22.45°, 24.80°, 25.01°, 25.45°, 26.19°, 26.61°, 27.85°, 28.15°, 28.79°, 29.35°, 29.78°, 30.13°, 30.51°, 31.29°, 31.61°, 31.92°, 32.45° and 35.41°. The error margin in 2θ of the characteristic peaks is ±0.2°.

2) The DSC thermogram of crystalline form B was analyzed and identified by using TA Q2000 differential scanning calorimetry (DSC) with a scan rate of 10° C./minute, comprising an endothermic peak at 165.8° C. The error margin in the melting peaks is ±3° C.

Example 4

The Preparation of Crystalline Form C

A 100 mL eggplant-shaped bottle was charged with 4[R, S]-ethyl 4-(2-bromo-4-fluorophenyl)-6-(morpholinomethyl)-2-(thiazol-2-yl)-1,4-dihydropyrimidine-5-carboxylate (5 g, 9.8 mmol, the compound was synthesized according to the procedures described in patent WO 2008/154817) and acetonitrile (50 mL). The suspension was heated to reflux until all solid had dissolved, and a solution of methanesulfonic acid (2.17 g, 22.5 mmol) in acetonitrile (5 mL) was added dropwise. The mixture was stirred for 3 hours under reflux. By cooling the reaction mixture to room temperature, crystals precipitated, and were collected by filtration, washed with acetonitrile and dried in a vacuum oven at 50° C. to give the product as a yellow solid (3.56 g, 60.0%).

The Identification of Crystalline Form C

1) The XRPD pattern of crystalline form C was analyzed and identified by using Empyrean X-ray powder diffraction (XRPD) with Cu-Kα radiation, having the following characteristic peaks expressed in degrees 2θ at 5.39°, 10.42°, 10.69°, 12.04°, 13.25°, 13.56°, 16.00°, 17.27°, 19.61°, 19.86°, 20.02°, 20.31°, 21.33°, 21.92°, 22.17°, 22.29°, 22.53°, 23.47°, 23.58°, 24.35°, 24.96°, 25.10°, 26.39°, 26.56°, 26.87°, 27.25°, 27.64°, 29.41°, 29.90°, 30.31°, 30.52°, 31.35°, 32.05°, 32.22°, 32.96°, 33.71°, 34.11°, 34.88°, 36.23° and 36.46°. The error margin in 2θ of the characteristic peaks is ±0.2°.

2) The DSC thermogram of crystalline form C was analyzed and identified by using TA Q2000 differential scanning calorimetry (DSC) with a scan rate of 10° C./minute, comprising an endothermic peak at 172.6° C. The error margin in the melting peaks is ±3° C.

Example 5

The Preparation of Crystalline Form G

A 250 mL eggplant-shaped bottle was charged with compound Z (30 g, 49.5 mmol) and ethylene glycol (30 mL). The suspension was heated at 80° C. until all solid had dissolved. It was then cooled to room temperature followed by adding 120 mL of ethylene glycol. The mixture was stirred for 12 hours at room temperature and then filtered. The solid was washed with petroleum ether and dried in a vacuum oven at 50° C. to give the product as a yellow solid (15 g, 42.2%).

The Identification of Crystalline Form G

1) The XRPD pattern of crystalline form G was analyzed and identified by using Empyrean X-ray powder diffraction (XRPD) with Cu-Kα radiation, having the following characteristic peaks expressed in degrees 2θ at 7.07°, 7.80°, 9.99°, 10.30°, 11.14°, 14.20°, 15.36°, 16.47°, 17.30°, 19.40°, 19.73°, 19.85°, 20.40°, 20.61°, 21.26°, 22.37°, 22.82°, 23.21°, 23.58°, 23.83°, 24.58°, 25.66°, 25.94°, 26.87°, 27.02°, 27.18°, 27.79°, 28.11°, 28.40°, 29.98°, 30.27°, 30.66°, 31.14°, 32.11°, 32.42°, 32.76°, 33.11° and 33.34°. The error margin in 2θ of the characteristic peaks is ±0.2°.

2) The DSC thermogram of crystalline form G was analyzed and identified by using TA Q2000 differential scanning calorimetry (DSC) with a scan rate of 10° C./minute, comprising an endothermic peak at 134.3° C. The error margin in the melting peaks is ±3° C.

Example 6

The Preparation of Crystalline Form H

A 250 mL eggplant-shaped bottle was charged with compound Z (30 g, 49.5 mmol) and 1-methyl-2-pyrrolidinone (30 mL). The suspension was heated at 80° C. until all solid had dissolved. It was then cooled to room temperature followed by adding 100 mL of diethyl ether. The mixture was stirred for 12 hours at room temperature and then filtered. The solid was washed with diethyl ether and dried in a vacuum oven at 50° C. to give the product as a yellow solid (18 g, 50.6%).

The Identification of Crystalline Form H

1) The XRPD pattern of crystalline form H was analyzed and identified by using Empyrean X-ray powder diffraction (XRPD) with Cu-Kα radiation, having the following characteristic peaks expressed in degrees 2θ at 7.58°, 10.29°, 12.00°, 14.78°, 15.83°, 16.49°, 17.69°, 18.32°, 19.07°, 19.24°, 19.93°, 20.13°, 20.78°, 21.33°, 21.48°, 21.88°, 22.35°, 22.60°, 23.37°, 23.77°, 24.40°, 24.58°, 24.76°, 25.59°, 25.82°, 26.01°, 26.58°, 27.15°, 27.31°, 27.49°, 27.78°, 29.28°, 29.77°, 30.17°, 31.69°, 31.98°, 32.30° and 33.28°. The error margin in 2θ of the characteristic peaks is ±0.2°.

2) The DSC thermogram of crystalline form H was analyzed and identified by using TA Q2000 differential scanning calorimetry (DSC) with a scan rate of 10° C./minute, comprising an endothermic peak at 132.1° C. The error margin in the melting peaks is ±3° C.

Example 7

The Preparation of Crystalline Form I

A 5000 mL eggplant-shaped bottle was charged with compound Z (300 g, 495 mmol) and water (3000 mL). The stirred suspension was heated at 50° C. until all solid had dissolved. It was further stirred for 1 hour at room temperature. The reaction mixture was then cooled slowly to 10° C., stirred for 12 hours and filtered. The solid was washed with water and dried in a vacuum oven at 50° C. to give the product as a yellow solid (250 g, 70.3%).

The Identification of Crystalline Form I

1) The XRPD pattern of crystalline form I was analyzed and identified by using Empyrean X-ray powder diffraction (XRPD) with Cu-Kα radiation, having the following characteristic peaks expressed in degrees 2θ at 4.41°, 9.26°, 9.41°, 10.13°, 11.25°, 12.64°, 13.04°, 17.59°, 18.29°, 20.17°, 20.29°, 21.37°, 21.72°, 21.90°, 22.15°, 22.50°, 23.76°, 23.90°, 24.59°, 24.99°, 25.71°, 26.32°, 26.95°, 27.09°, 27.66°, 27.90°, 28.54°, 29.10°, 29.68°, 30.53°, 30.93°, 32.18°, 33.03° and 33.56°. The error margin in 2θ of the characteristic peaks is ±0.2°.

2) The DSC thermogram of crystalline form I was analyzed and identified by using TA Q2000 differential scanning calorimetry (DSC) with a scan rate of 10° C./minute, comprising an endothermic peak at 82.0° C. The error margin in the melting peaks is ±3° C.

Example 8

Solubility Test

About 600 mg of a crystalline form sample was added to water (2 mL). The dissolution of the sample was obtained with ultrasonic vibration at 25±5° C. No visible solute particles mean that the sample has a complete dissolution in water; whereas visible solute particles mean that the sample precipitates in water. The test results of the sample are shown in Table 1.

TABLE 1

| Dissolution of crystalline forms B and C | |
|---|---|
| crystalline forms | dissolubility of samples (300 mg/mL) |
| form B | completely dissolved, some sample precipitated after 1 hour |
| form C | completely dissolved, no sample precipitated after 4 hours |

The data in Table 1 show that both of crystalline forms B and C have good solubility in water.

Example 9

Stability Test

A crystalline form sample was put in a watch glass in the form of a thin layer of ≤5 mm. The stability test was conducted under different conditions: high temperature (60±2° C.) for 30 days, accelerated condition (40±2° C., 75%±5% humidity) for 30 days, mediated condition (30±2° C., 65%±5% humidity) for 30 days, high humidity (25±2° C., 90%±5%) for 10 days and illumination condition (visible light 4500 lx±500 lx with ultraviolet light not lower than 0.7 W·h/m², 25±2° C., 60%±5% relative humidity) for 10 days respectively. The impurity contents of crystalline forms B and C were determined at various time points (0, 10, 20, and 30 days) by high performance liquid chromatography (HPLC) with peak area normalization. The data are shown in Tables 2 and 3.

TABLE 2

The impurity content of crystalline form B by HPLC

|  | 0 day | 10 days | 20 days | 30 days |
| --- | --- | --- | --- | --- |
| high temperature | 0.06% | 0.13% | 0.20% | 0.24% |
| accelerated condition | 0.06% | 0.09% | 0.08% | 0.10% |
| mediated condition | 0.06% | 0.10% | 0.13% | 0.12% |
| high humidity | 0.06% | 0.06% | N/A | N/A |
| illumination condition | 0.06% | 0.12% | N/A | N/A |

N/A - The sample was not tested at these conditions.

TABLE 3

The impurity content of crystalline form C by HPLC

|  | 0 day | 10 days | 20 days | 30 days |
| --- | --- | --- | --- | --- |
| high temperature | 0.03% | 0.06% | 0.03% | 0.03% |
| accelerated condition | 0.03% | 0.04% | 0.04% | 0.04% |
| mediated condition | 0.03% | 0.03% | 0.03% | 0.03% |
| high humidity | 0.03% | 0.04% | N/A | N/A |
| illumination condition | 0.03% | 0.03% | N/A | N/A |

N/A - The sample was not tested in these conditions.

The results in Tables 2 and 3 indicate that crystalline forms B and C did not degrade or change under the experimental conditions specified. The impurity contents in crystalline forms B and C remained unchanged at these conditions. Both of crystalline forms B and C have good stability, which meet the official requirements The foregoing has described the invention including basic instructions. Any alterations that would be apparent to the skilled person are within the scope of the invention.

The invention claimed is:

1. A crystalline form of the compound of formula (I):

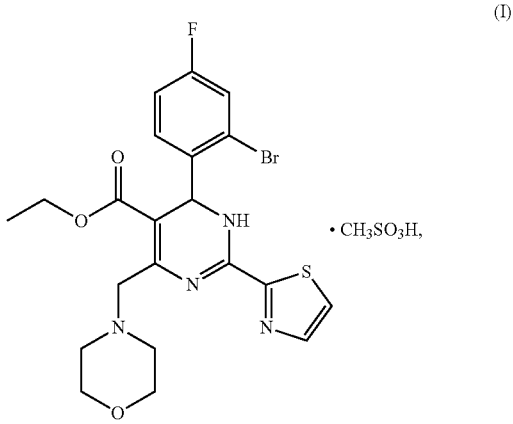

(I)

or a tautomer or a combination thereof, wherein the crystalline form is form A, form B, form C, form G, form H, form I or a combination thereof.

2. The crystalline form of claim 1, wherein the crystalline form is form A having an X-ray powder diffraction (XRPD) pattern comprising peaks expressed in degrees 2θ at 6.57°±0.2°, 13.13°±0.2°, 13.38°±0.2°, 19.73°±0.2°, 20.18°±0.2°, 20.90°±0.2°, 24.90°±0.2°, 26.63°±0.2° and 29.01°±0.2°.

3. The crystalline form of claim 1, wherein the crystalline form is form A having an X-ray powder diffraction (XRPD) pattern comprising peaks expressed in degrees 2θ at 6.57°±0.2°, 13.13°±0.2°, 13.38°±0.2°, 19.73°±0.2°, 20.18°±0.2°, 20.90°±0.2°, 22.43°±0.2°, 24.38°±0.2°, 24.90°±0.2°, 26.63°±0.2°, 27.93°±0.2° and 29.01°±0.2°.

4. The crystalline form of claim 1, wherein the crystalline form is form A having an X-ray powder diffraction (XRPD) pattern comprising peaks expressed in degrees 2θ at 6.57°±0.2°, 9.73°±0.2°, 11.14°±0.2°, 13.13°±0.2°, 13.38°±0.2°, 19.73°±0.2°, 20.18°±0.2°, 20.90°±0.2°, 22.43°±0.2°, 23.20°±0.2°, 24.38°±0.2°, 24.90°±0.2°, 26.63°±0.2°, 27.93°±0.2°, 29.01°±0.2°, 29.84°±0.2°, 30.78°±0.2° and 31.68°±0.2°.

5. The crystalline form of claim 1, wherein the crystalline form is form A having a differential scanning calorimetry (DSC) thermogram comprising an endothermic peak at about 162.3° C.±3° C.

6. The crystalline form of claim 1, wherein the crystalline form is form B having an X-ray powder diffraction (XRPD) pattern comprising peaks expressed in degrees 2θ at 6.68°±0.2°, 13.39°±0.2°, 19.65°±0.2°, 20.26°±0.2°, 22.45°±0.2°, 24.80°±0.2°, 25.01°±0.2°, 26.19°±0.2°, 26.61°±0.2° and 28.79°±0.2°.

7. The crystalline form of claim 1, wherein the crystalline form is form B having an X-ray powder diffraction (XRPD) pattern comprising peaks expressed in degrees 2θ at 6.68°±0.2°, 9.77°±0.2°, 9.98°±0.2°, 11.88°±0.2°, 13.39°±0.2°, 16.65°±0.2°, 17.66°±0.2°, 19.08°±0.2°, 19.65°±0.2°, 20.26°±0.2°, 20.81°±0.2°, 20.97°±0.2°, 22.45°±0.2°, 24.80°±0.2°, 25.01°±0.2°, 26.19°±0.2°, 26.61°±0.2°, 28.79°±0.2°, 29.78°±0.2°, 30.13°±0.2°, 31.61° 0.2°, 31.92°±0.2° and 32.45°±0.2°.

8. The crystalline form of claim 1, wherein the crystalline form is form B having an X-ray powder diffraction (XRPD) pattern comprising peaks expressed in degrees 2θ at 6.68°±0.2°, 9.77°±0.2°, 9.98°±0.2°, 11.88°±0.2°, 13.39°±0.2°, 14.62°±0.2°, 16.65°±0.2°, 17.66°±0.2°, 19.08°±0.2°, 19.65°±0.2°, 20.26°±0.2°, 20.81°±0.2°, 20.97°±0.2°, 22.07°±0.2°, 22.45°±0.2°, 24.80°±0.2°, 25.01°±0.2°, 25.45°±0.2°, 26.19°±0.2°, 26.61°±0.2°, 27.85°±0.2°, 28.15°±0.2°, 28.79°±0.2°, 29.35°±0.2°, 29.78°±0.2°, 30.13°±0.2°, 30.51°±0.2°, 31.29°±0.2°, 31.61°±0.2°, 31.92°±0.2°, 32.45°±0.2° and 35.41°±0.2°.

9. The crystalline form of claim 1, wherein the crystalline form is form B having a differential scanning calorimetry (DSC) thermogram comprising an endothermic peak at about 165.8° C.±3° C.

10. The crystalline form of claim 1, wherein the crystalline form is form C having an X-ray powder diffraction (XRPD) pattern comprising peaks expressed in degrees 2θ at 5.39°±0.2°, 13.25°±0.2°, 16.00°±0.2°, 17.27°±0.2°, 21.33°±0.2°, 21.92°±0.2°, 22.53°±0.2°, 23.47°±0.2°, 26.56°±0.2°, 26.87°±0.2°, 29.41°±0.2° and 32.22°±0.2°.

11. The crystalline form of claim 1, wherein the crystalline form is form C having an X-ray powder diffraction (XRPD) pattern comprising peaks expressed in degrees 2θ at 5.39°±0.2°, 13.25°±0.2°, 16.00°±0.2°, 17.27°±0.2°, 20.31°±0.2°, 21.33°±0.2°, 21.92°±0.2°, 22.53°±0.2°, 23.47°±0.2°, 23.58°±0.2°, 26.56°±0.2°, 26.87°±0.2°, 29.41°±0.2°, 30.52°±0.2°, 31.35°±0.2°, 32.05°±0.2° and 32.22°±0.2°.

12. The crystalline form of claim 1, wherein the crystalline form is form C having an X-ray powder diffraction (XRPD) pattern comprising peaks expressed in degrees 2θ at 5.39°±0.2°, 10.42°±0.2°, 10.69°±0.2°, 12.04°±0.2°, 13.25°±0.2°, 13.56°±0.2°, 16.00°±0.2°, 17.27°±0.2°, 19.61°±0.2°, 19.86°±0.2°, 20.02°±0.2°, 20.31°±0.2°, 21.33°±0.2°, 21.92°±0.2°, 22.17°±0.2°, 22.29°±0.2°, 22.53°±0.2°, 23.47°±0.2°, 23.58°±0.2°, 24.35°±0.2°, 24.96°±0.2°, 25.10°±0.2°, 26.39°±0.2°, 26.56°±0.2°, 26.87°±0.2°, 27.25°±0.2°, 27.64°±0.2°, 29.41°±0.2°, 29.90°±0.2°, 30.31°±0.2°, 30.52°±0.2°, 31.35°±0.2°, 32.05°±0.2°, 32.22°±0.2°, 32.96°±0.2°, 33.71°±0.2°, 34.11°±0.2°, 34.88°±0.2°, 36.23°±0.2° and 36.46°±0.2°.

13. The crystalline form of claim 1, wherein the crystalline form is form C having a differential scanning calorimetry (DSC) thermogram comprising an endothermic peak at about 172.6° C.±3° C.

14. The crystalline form of claim 1, wherein the crystalline form is form G having an X-ray powder diffraction (XRPD) pattern comprising peaks expressed in degrees 2θ at 16.47°±0.2°, 19.40°±0.2°, 20.61°±0.2°, 22.37°±0.2°, 22.82°±0.2°, 23.21°±0.2°, 25.66°±0.2°, 25.94°±0.2°, 26.87°±0.2°, 27.02°±0.2°, 28.11°±0.2° and 30.27°±0.2°.

15. The crystalline form of claim 1, wherein the crystalline form is form G having an X-ray powder diffraction (XRPD) pattern comprising peaks expressed in degrees 2θ at 9.99°±0.2°, 10.30°±0.2°, 16.47°±0.2°, 17.30°±0.2°, 19.40°±0.2°, 20.61°±0.2°, 21.26°±0.2°, 22.37°±0.2°, 22.82°±0.2°, 23.21°±0.2°, 23.58°±0.2°, 25.66°±0.2°, 25.94°±0.2°, 26.87°±0.2°, 27.02°±0.2°, 27.18°±0.2°, 28.11°±0.2°, 28.40°±0.2°, 29.98°±0.2°, 30.27°±0.2°, 31.14°±0.2°, 32.42°±0.2°, 33.11°±0.2° and 33.34°±0.2°.

16. The crystalline form of claim 1, wherein the crystalline form is form G having an X-ray powder diffraction (XRPD) pattern comprising peaks expressed in degrees 2θ at 7.07°±0.2°, 7.80°±0.2°, 9.99°±0.2°, 10.30°±0.2°, 11.14°±0.2°, 14.20°±0.2°, 15.36°±0.2°, 16.47°±0.2°, 17.30°±0.2°, 19.40°±0.2°, 19.73°±0.2°, 19.85°±0.2°, 20.40°±0.2°, 20.61°±0.2°, 21.26°±0.2°, 22.37°±0.2°, 22.82°±0.2°, 23.21°±0.2°, 23.58°±0.2°, 23.83°±0.2°, 24.58°±0.2°, 25.66°±0.2°, 25.94°±0.2°, 26.87°±0.2°, 27.02°±0.2°, 27.18°±0.2°, 27.79°±0.2°, 28.11°±0.2°, 28.40°±0.2°, 29.98°±0.2°, 30.27°±0.2°, 30.66°±0.2°, 31.14°±0.2°, 32.11°±0.2°, 32.42°±0.2°, 32.76°±0.2°, 33.11°±0.2° and 33.34°±0.2°.

17. The crystalline form of claim 1, wherein the crystalline form is form G having a differential scanning calorimetry (DSC) thermogram comprising an endothermic peak at about 134.3° C.±3° C.

18. The crystalline form of claim 1, wherein the crystalline form is form H having an X-ray powder diffraction (XRPD) pattern comprising peaks expressed in degrees 2θ at 7.58°±0.2°, 10.29°±0.2°, 12.00°±0.2°, 19.07°±0.2°, 19.93°±0.2°, 20.78°±0.2°, 21.33°±0.2°, 21.48°±0.2°, 24.76°±0.2°, 25.59°±0.2°, 25.82°±0.2°, 26.01°±0.2° and 26.58°±0.2°.

19. The crystalline form of claim 1, wherein the crystalline form is form H having an X-ray powder diffraction (XRPD) pattern comprising peaks expressed in degrees 2θ at 7.58°±0.2°, 10.29°±0.2°, 12.00°±0.2°, 14.78°±0.2°, 17.69°±0.2°, 18.32°±0.2°, 19.07°±0.2°, 19.93°±0.2°, 20.13°±0.2°, 20.78°±0.2°, 21.33°±0.2°, 21.48°±0.2°, 22.60°±0.2°, 24.40°±0.2°, 24.58°±0.2°, 24.76°±0.2°, 25.59°±0.2°, 25.82°±0.2°, 26.01°±0.2°, 26.58°±0.2°, 27.15°±0.2°, 27.31°±0.2°, 27.49°±0.2°, 27.78°±0.2°, 31.69°±0.2° and 31.98°±0.2°.

20. The crystalline form of claim 1, wherein the crystalline form is form H having an X-ray powder diffraction (XRPD) pattern comprising peaks expressed in degrees 2θ at 7.58°±0.2°, 10.29°±0.2°, 12.00°±0.2°, 14.78°±0.2°, 15.83°±0.2°, 16.49°±0.2°, 17.69°±0.2°, 18.32°±0.2°, 19.07°±0.2°, 19.24°±0.2°, 19.93°±0.2°, 20.13°±0.2°, 20.78°±0.2°, 21.33°±0.2°, 21.48°±0.2°, 21.88°±0.2°, 22.35°±0.2°, 22.60°±0.2°, 23.37°±0.2°, 23.77°±0.2°, 24.40°±0.2°, 24.58°±0.2°, 24.76°±0.2°, 25.59°±0.2°, 25.82°±0.2°, 26.01°±0.2°, 26.58°±0.2°, 27.15°±0.2°, 27.31°±0.2°, 27.49°±0.2°, 27.78°±0.2°, 29.28°±0.2°, 29.77°±0.2°, 30.17°±0.2°, 31.69°±0.2°, 31.98°±0.2°, 32.30°±0.2° and 33.28°±0.2°.

21. The crystalline form of claim 1, wherein the crystalline form is form H having a differential scanning calorimetry (DSC) thermogram comprising an endothermic peak at about 132.1° C.±3° C.

22. The crystalline form of claim 1, wherein the crystalline form is form I having an X-ray powder diffraction (XRPD) pattern comprising peaks expressed in degrees 2θ at 9.41°±0.2°, 17.59°±0.2°, 21.37°±0.2°, 21.72°±0.2°, 22.15°±0.2°, 22.50°±0.2°, 23.90°±0.2°, 24.59°±0.2°, 24.99°±0.2°, 26.32°±0.2°, 27.09°±0.2°, 29.68°±0.2° and 30.53°±0.2°.

23. The crystalline form of claim 1, wherein the crystalline form is form I having an X-ray powder diffraction (XRPD) pattern comprising peaks expressed in degrees 2θ at 9.41°±0.2°, 10.13°±0.2°, 12.64°±0.2°, 13.04°±0.2°, 17.59°±0.2°, 21.37°±0.2°, 21.72°±0.2°, 21.90°±0.2°, 22.15°±0.2°, 22.50°±0.2°, 23.76°±0.2°, 23.90°±0.2°, 24.59°±0.2°, 24.99°±0.2°, 26.32°±0.2°, 26.95°±0.2°, 27.09°±0.2°, 27.90°±0.2°, 28.54°±0.2°, 29.10°±0.2°, 29.68°±0.2°, 30.53°±0.2°, 32.18°±0.2° and 33.03°±0.2°.

24. The crystalline form of claim 1, wherein the crystalline form is form I having an X-ray powder diffraction (XRPD) pattern comprising peaks expressed in degrees 2θ at 4.41°±0.2°, 9.26°±0.2°, 9.41°±0.2°, 10.13°±0.2°, 11.25°±0.2°, 12.64°±0.2°, 13.04°±0.2°, 17.59°±0.2°, 18.29°±0.2°, 20.17°±0.2°, 20.29°±0.2°, 21.37°±0.2°, 21.72°±0.2°, 21.90°±0.2°, 22.15°±0.2°, 22.50°±0.2°, 23.76°±0.2°, 23.90°±0.2°, 24.59°±0.2°, 24.99°±0.2°, 25.71°±0.2°, 26.32°±0.2°, 26.95°±0.2°, 27.09°±0.2°, 27.66°±0.2°, 27.90°±0.2°, 28.54°±0.2°, 29.10°±0.2°, 29.68°±0.2°, 30.53°±0.2°, 30.93°±0.2°, 32.18°±0.2°, 33.03°±0.2° and 33.56°±0.2°.

25. The crystalline form of claim 1, wherein the crystalline form is form I having a differential scanning calorimetry (DSC) thermogram comprising an endothermic peak at about 82.0° C.±3° C.

Figure 2:
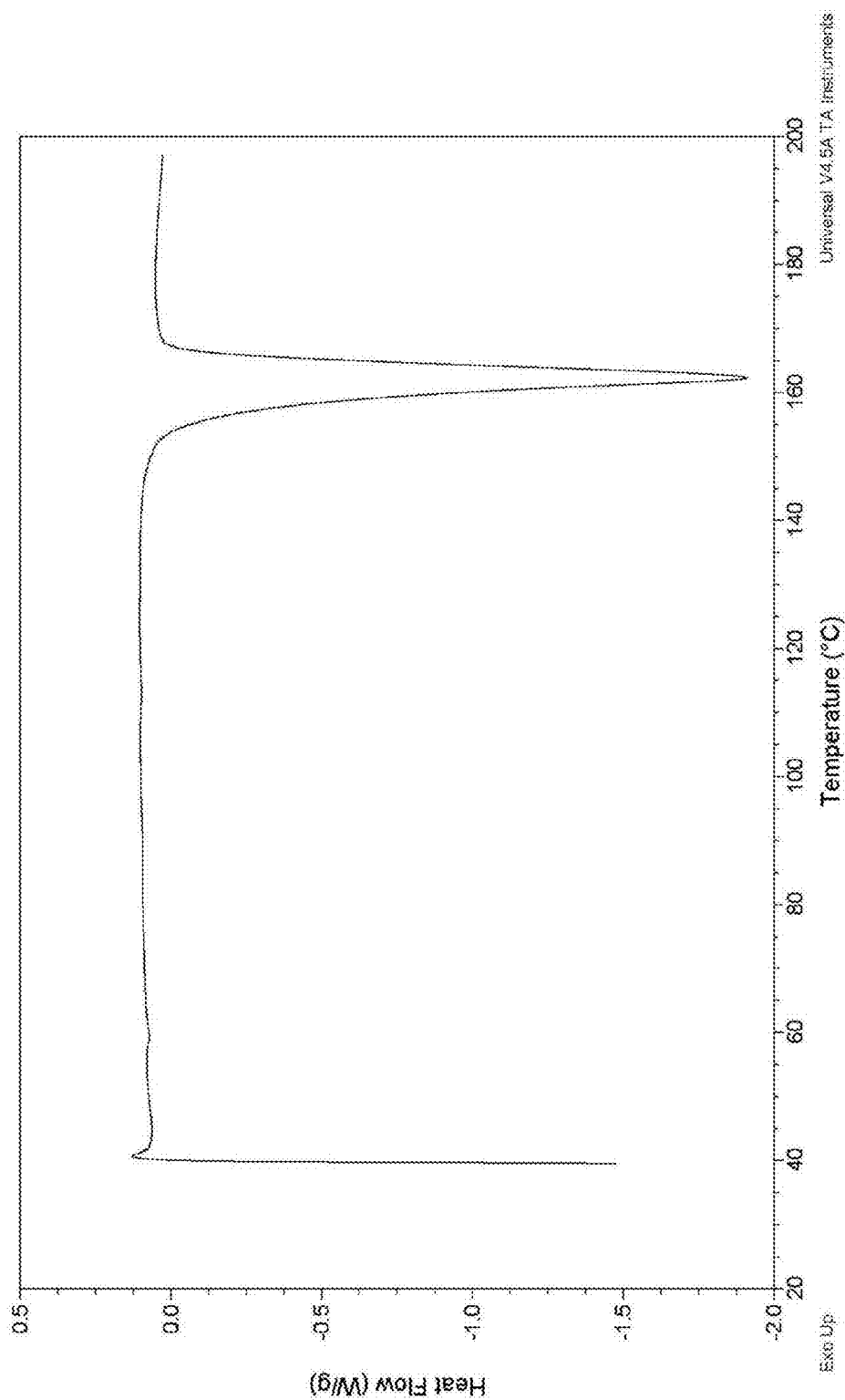
FIG. 2 shows the differential scanning calorimetry (DSC) thermogram of the crystalline form A of dihydropyrimidine derivative which is prepared according to the present invention.
Figure 4:
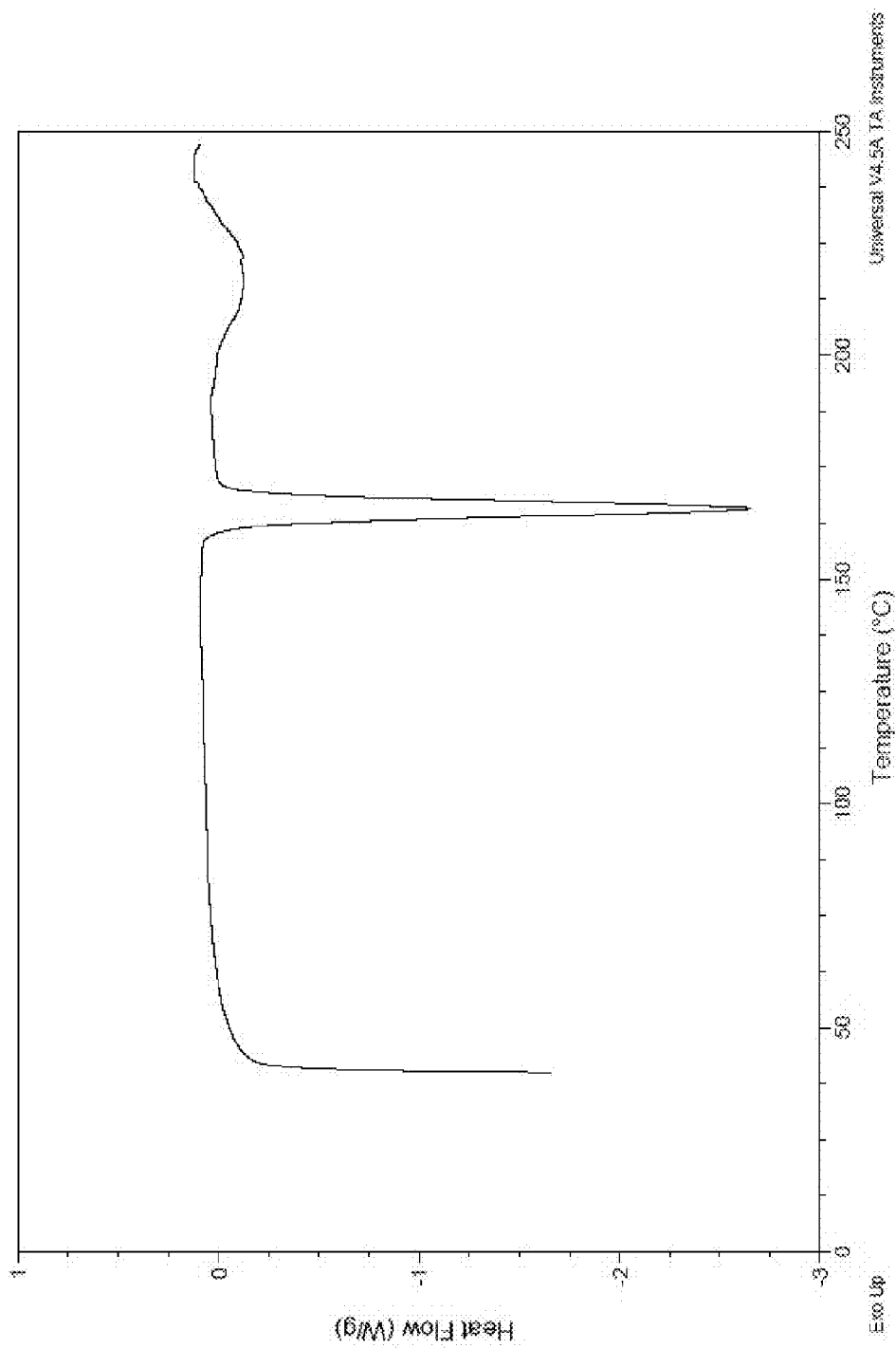
FIG. 4 shows the differential scanning calorimetry (DSC) thermogram of the crystalline form B of dihydropyrimidine derivative which is prepared according to the present invention.
Figure 6:
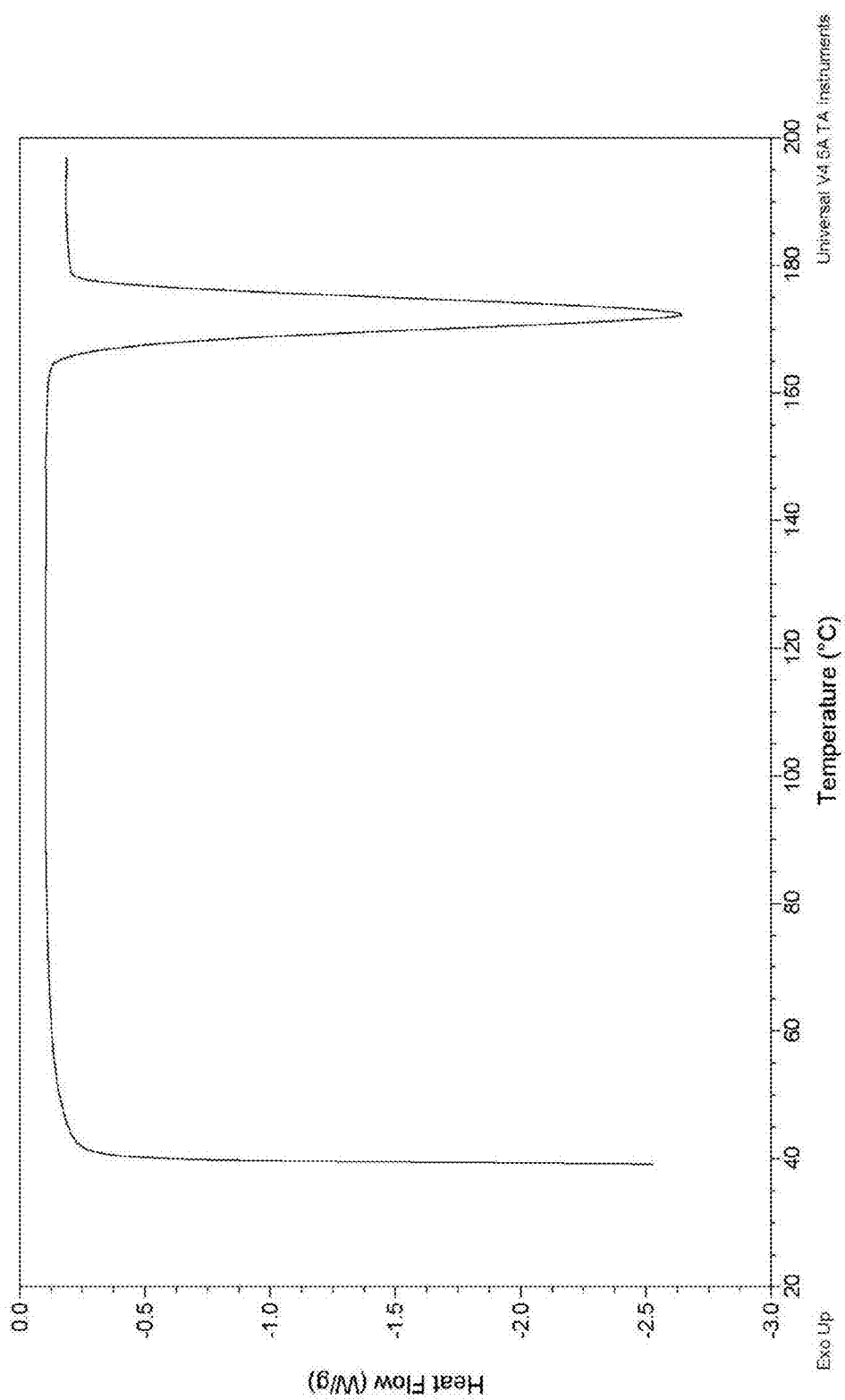
FIG. 6 shows the differential scanning calorimetry (DSC) thermogram of the crystalline form C of dihydropyrimidine derivative which is prepared according to the present invention.
Figure 8:
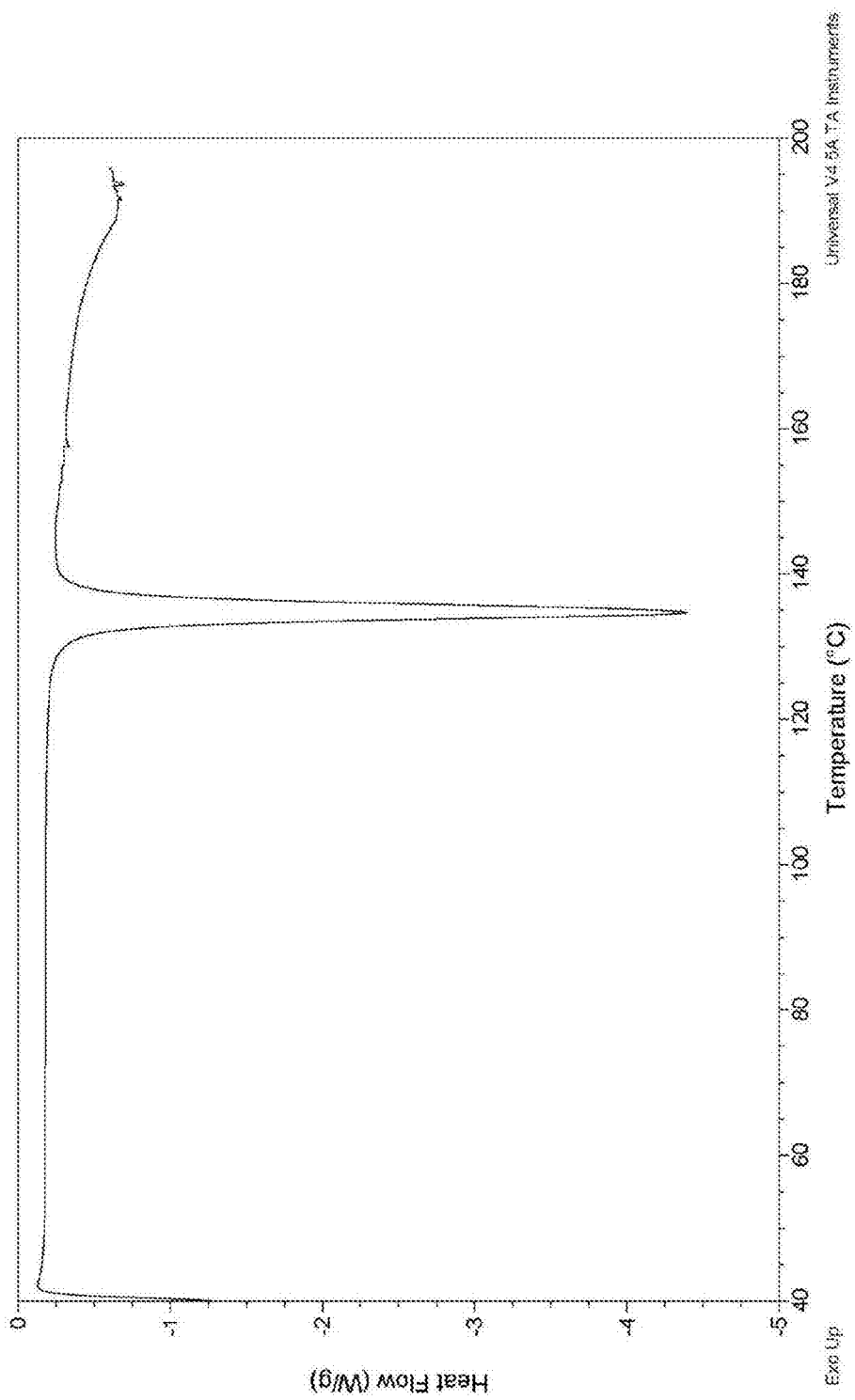
FIG. 8 shows the differential scanning calorimetry (DSC) thermogram of the crystalline form G of dihydropyrimidine derivative which is prepared according to the present invention.
Figure 10:
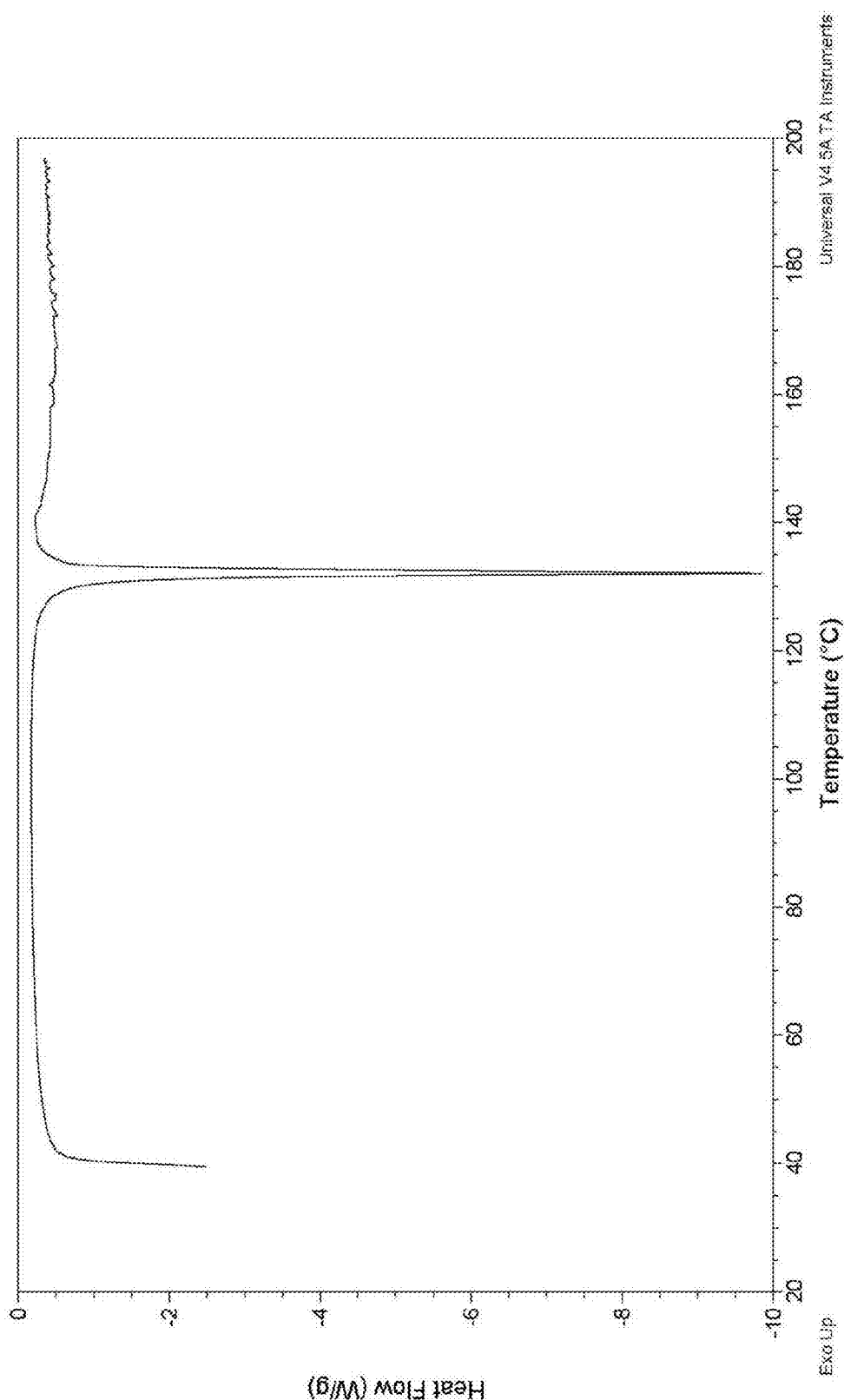
FIG. 10 shows the differential scanning calorimetry (DSC) thermogram of the crystalline form H of dihydropyrimidine derivative which is prepared according to the present invention.
Figure 12:
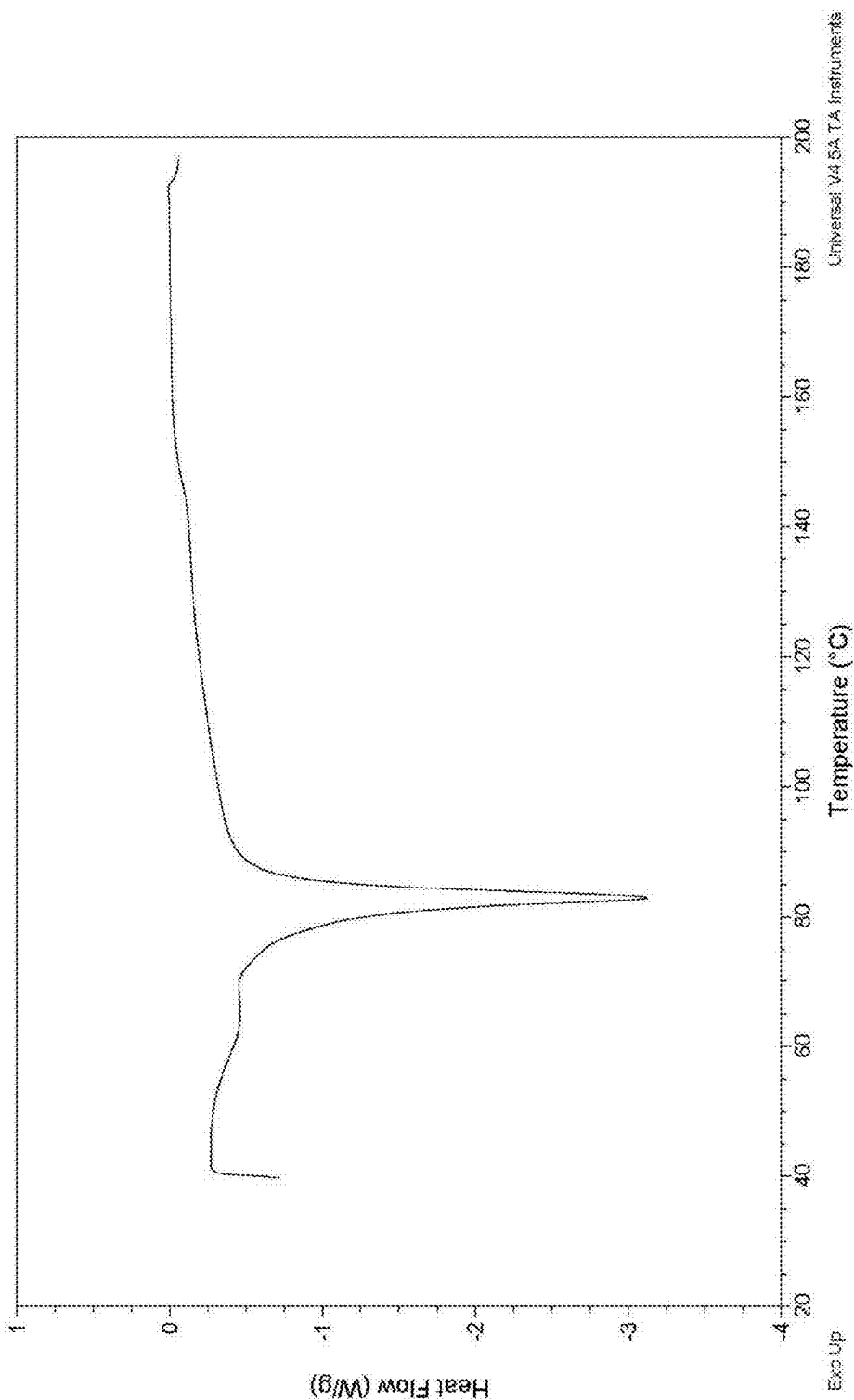
FIG. 12 shows the differential scanning calorimetry (DSC) thermogram of the crystalline form I of dihydropyrimidine derivative which is prepared according to the present invention.

26. The crystalline form of claim 1, wherein the crystalline form is form A having a differential scanning calorimetry (DSC) thermogram substantially the same as shown in FIG. 2;
  wherein the crystalline form is form B having a differential scanning calorimetry (DSC) thermogram substantially the same as shown in FIG. 4;
  wherein the crystalline form is form C having a differential scanning calorimetry (DSC) thermogram substantially the same as shown in FIG. 6;
  wherein the crystalline form is form G having a differential scanning calorimetry (DSC) thermogram substantially the same as shown in FIG. 8;
  wherein the crystalline form is form H having a differential scanning calorimetry (DSC) thermogram substantially the same as shown in FIG. 10; or
  wherein the crystalline form is form I having a differential scanning calorimetry (DSC) thermogram substantially the same as shown in FIG. 12.

27. A pharmaceutical composition comprising the crystalline form of claim 1; and a pharmaceutically acceptable carrier, excipient, diluent, adjuvant, vehicle or a combination thereof.

Figure 3:
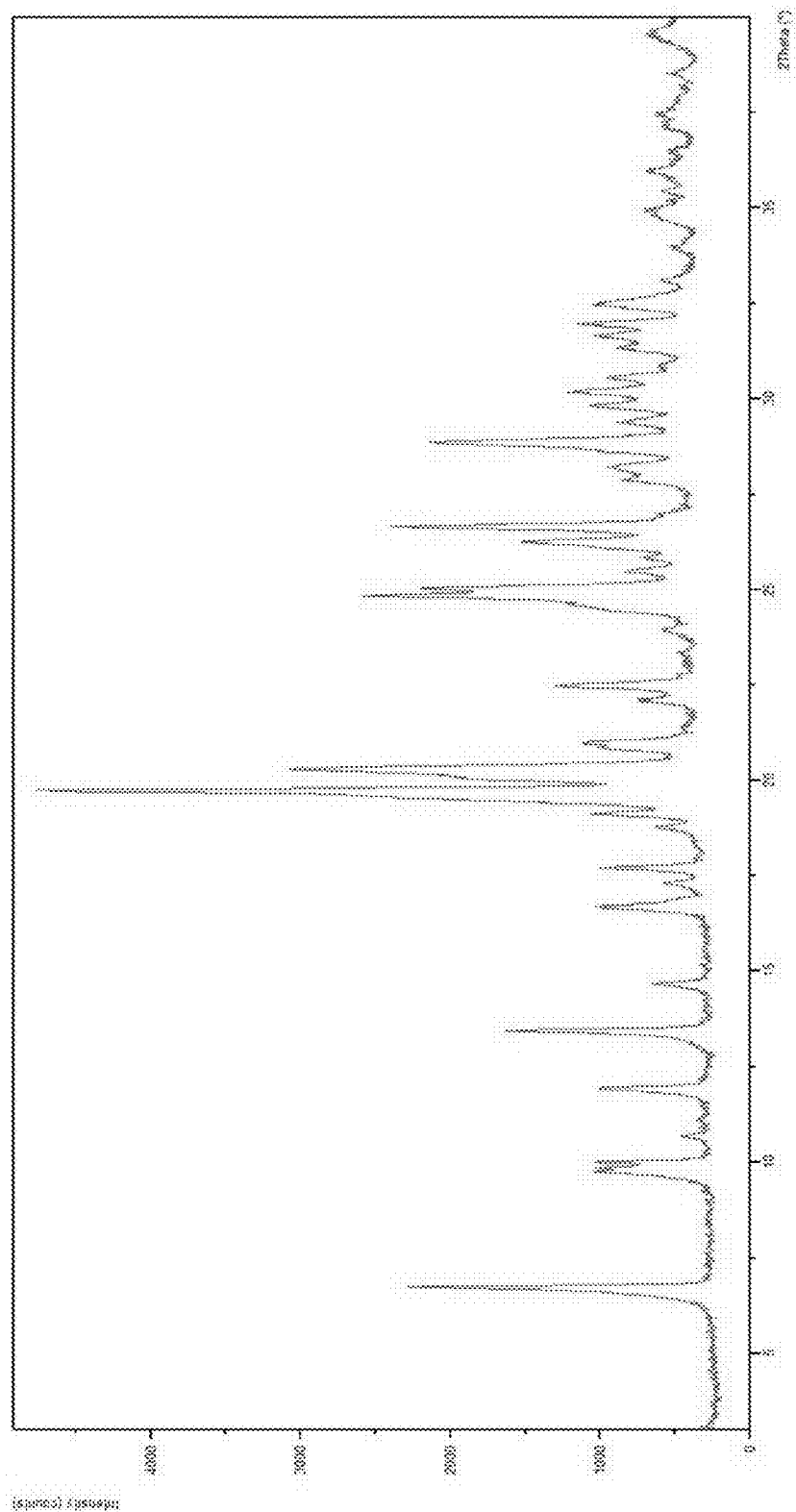
FIG. 3 shows the X-ray powder diffraction (XRPD) pattern of the crystalline form B of dihydropyrimidine derivative which is prepared according to the present invention.
Figure 5:
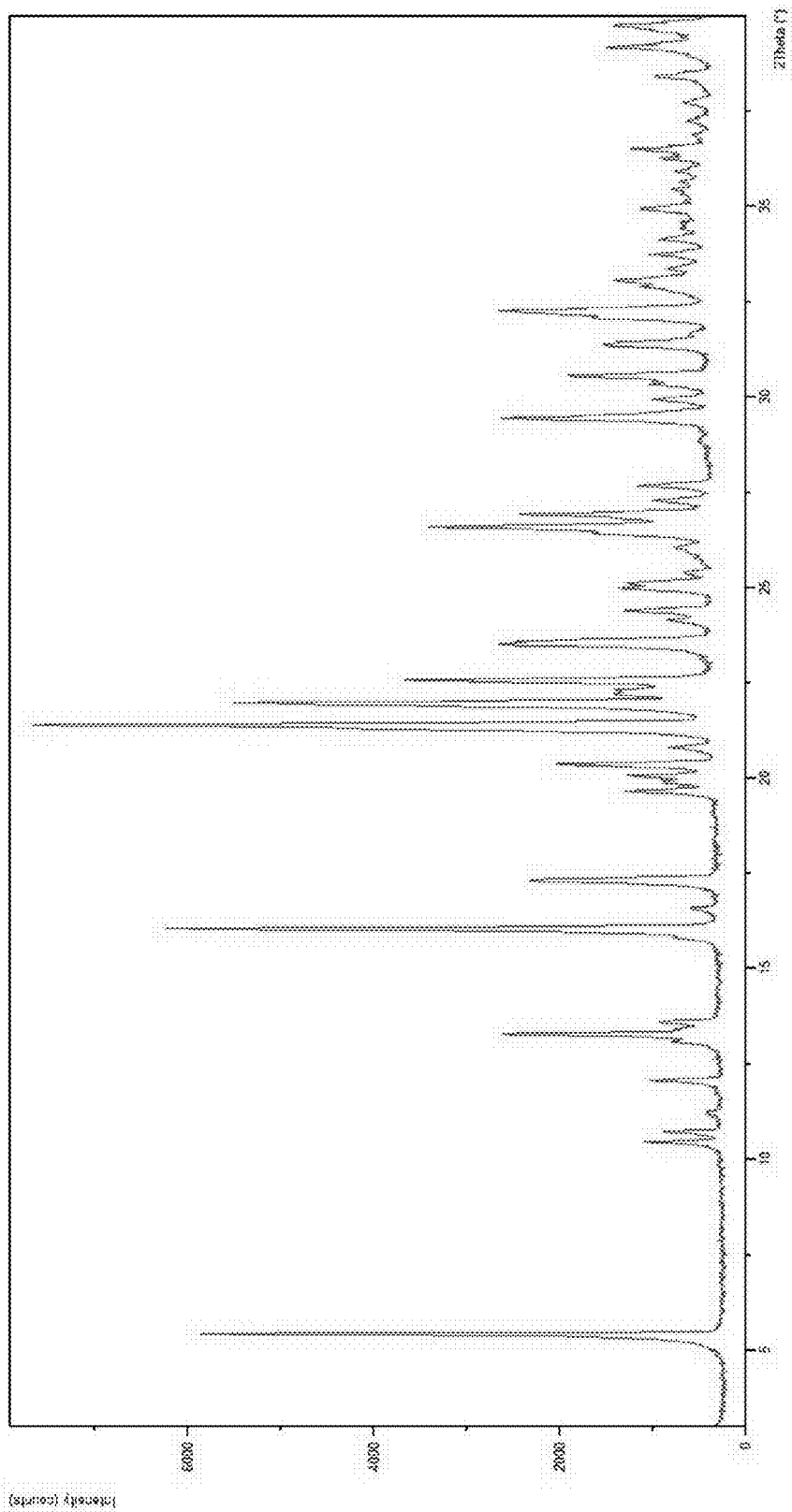
FIG. 5 shows the X-ray powder diffraction (XRPD) pattern of the crystalline form C of dihydropyrimidine derivative which is prepared according to the present invention.
Figure 7:
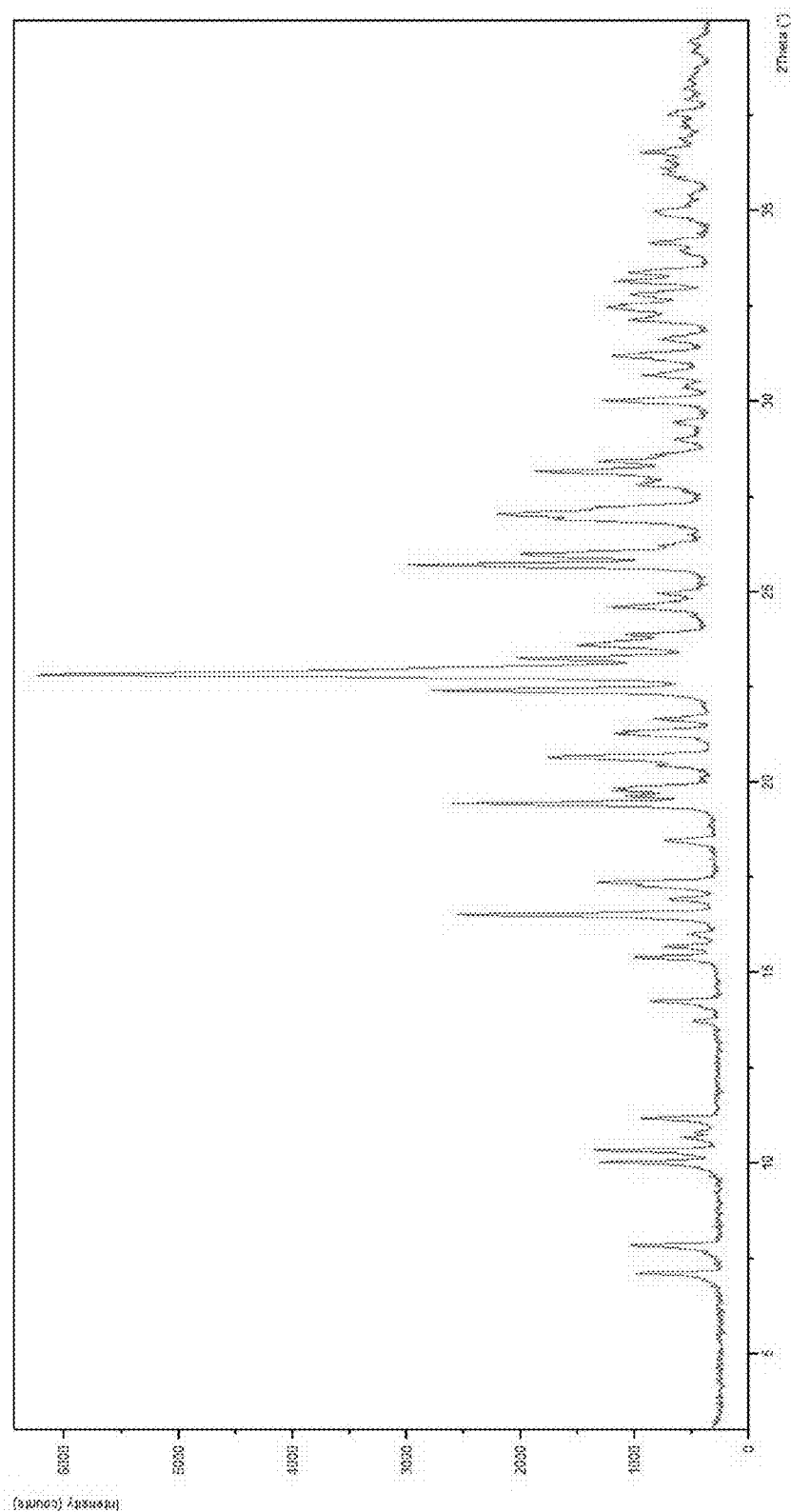
FIG. 7 shows the X-ray powder diffraction (XRPD) pattern of the crystalline form G of dihydropyrimidine derivative which is prepared according to the present invention.
Figure 9:
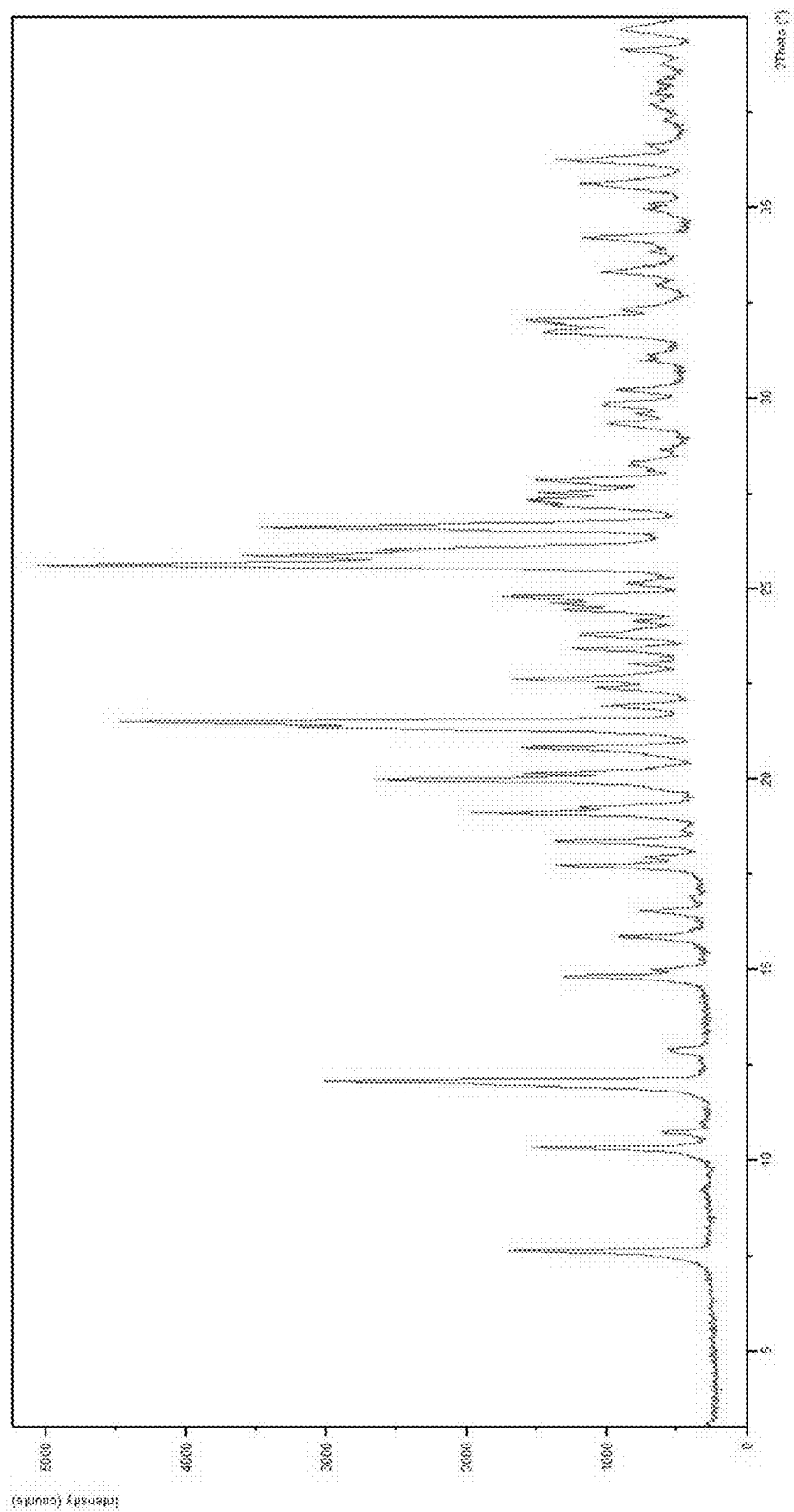
FIG. 9 shows the X-ray powder diffraction (XRPD) pattern of the crystalline form H of dihydropyrimidine derivative which is prepared according to the present invention.
Figure 11:
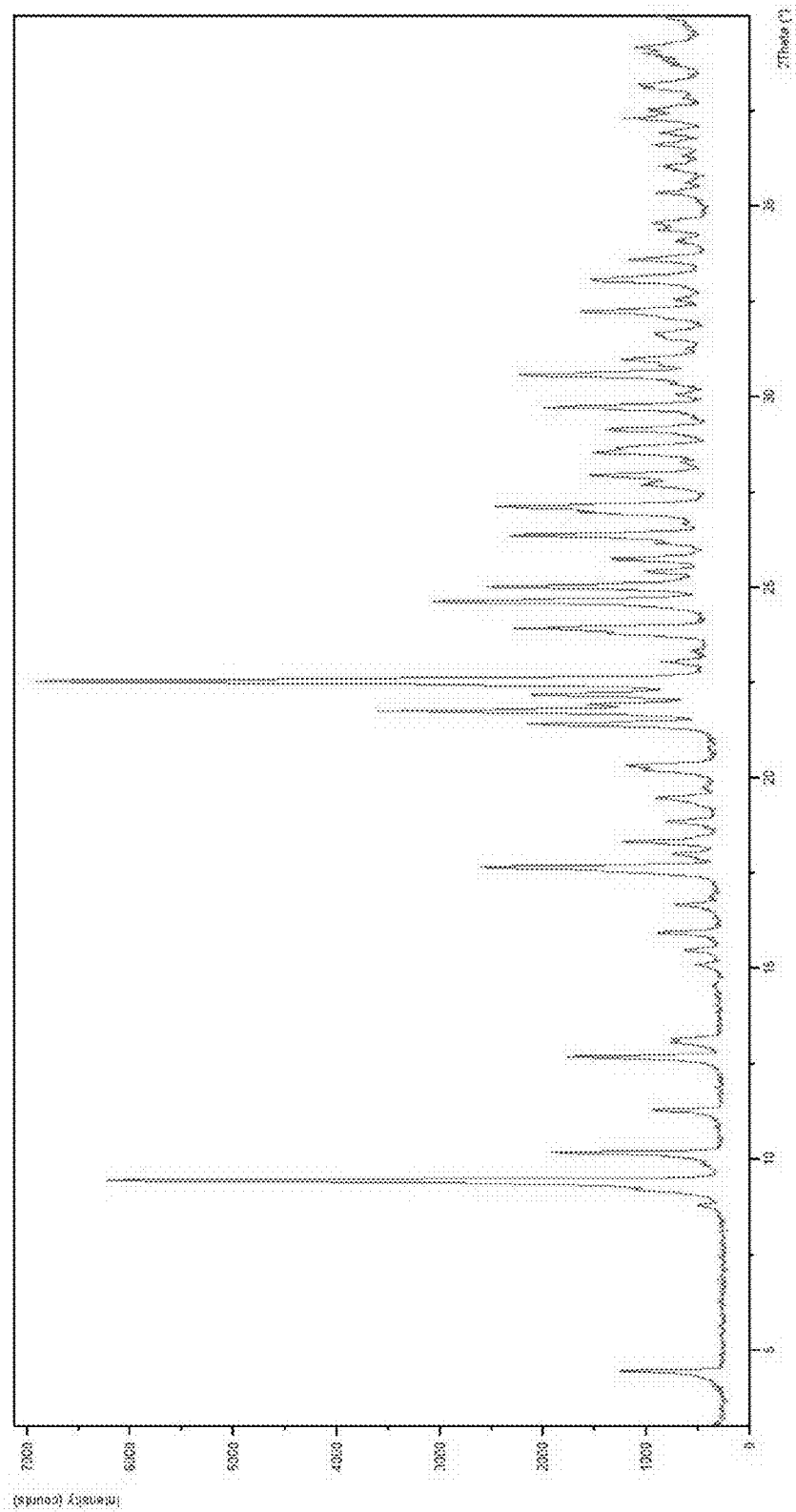
FIG. 11 shows the X-ray powder diffraction (XRPD) pattern of the crystalline form I of dihydropyrimidine derivative which is prepared according to the present invention.

28. The crystalline form of claim 1, wherein the crystalline form is form A having an X-ray powder diffraction (XRPD) pattern substantially the same as shown in FIG. 1;

wherein the crystalline form is form B having an X-ray powder diffraction (XRPD) pattern substantially the same as shown in FIG. 3;

wherein the crystalline form is form C having an X-ray powder diffraction (XRPD) pattern substantially the same as shown in FIG. 5;

wherein the crystalline form is form G having an X-ray powder diffraction (XRPD) pattern substantially the same as shown in FIG. 7;

wherein the crystalline form is form H having an X-ray powder diffraction (XRPD) pattern substantially the same as shown in FIG. 9; or wherein the crystalline form is form I having an X-ray powder diffraction (XRPD) pattern substantially the same as shown in FIG. 11.

* * * * *